United States Patent
Liu et al.

(10) Patent No.: US 10,971,249 B2
(45) Date of Patent: Apr. 6, 2021

(54) SYSTEMS AND METHODS FOR OFF-TARGET SEQUENCE DETECTION

(71) Applicant: ILLUMINA, INC., San Diego, CA (US)

(72) Inventors: Honglei Liu, Goleta, CA (US); Jocelyne Bruand, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 456 days.

(21) Appl. No.: 15/705,079

(22) Filed: Sep. 14, 2017

(65) Prior Publication Data

US 2018/0075186 A1 Mar. 15, 2018

Related U.S. Application Data

(60) Provisional application No. 62/395,288, filed on Sep. 15, 2016.

(51) Int. Cl.
*G16B 30/00* (2019.01)

(52) U.S. Cl.
CPC .................................. *G16B 30/00* (2019.02)

(58) Field of Classification Search
None
See application file for complete search history.

(56) References Cited

PUBLICATIONS

"How to: Design PCR primers and check them for specificity", NCBI website, www.ncbi.nlm.nih.gov, visited Sep. 3, 2016.
"K-mer", Wikipedia, Wikipedia.org, 5 pages., Sep. 3, 2016.
"Lecture 26: Indexing and the k-mer index", Johns Hopkins University, courrsera.org, visited Sep. 3, 2016, 4 pages.
"Lecture 30: Variations on k-mer indexes", Johns Hopkins University, courrsera.org, visited Sep. 3, 2016, 4 pages.
Gardner, et al., "Simulate_PCR for amplicon prediction and annotation from multiplex, degenerate primers and probes", BMC Bioinformatics, , available at http://www.biomedcentral.com/1471-2105/15/237, 2014, 15:237.
Qu, "MFEprimer—2.0 Manual", github.com, 8 pages, Jul. 13, 2015.
Shen, et al., "MPprimer: a program for reliable multiplex PCR primer design", BMC Bioinformatics 3010 11:143, DOI: 10.1186/1471-2105-11-143,, Mar. 18, 2019.
Valimaki, et al., "Scalable and Versatile k-mer Indexing for High-Throughput Sequencing Data", LIRMM Research Report, International Symposium on Bioinformatics Research and Applications (ISBRA), 17 pages., Mar. 23, 2017.
Ye, et al., "Primer-BLAST: A tool to design target-specific primers for polymerase chain reaction", BMC Bioinformatics 2012, 13:134, DOI: 10.1186/1471-2105-13-134, 13 pages, 2012.

*Primary Examiner* — Joseph Woitach
(74) *Attorney, Agent, or Firm* — Fletcher Yoder, P.C.

(57) ABSTRACT

A computer-implemented method, computer system and computer-readable medium for identifying off-target matches from a set of candidate primer sequences on a genome reference sequence can include: receiving onto a data storage unit a plurality of candidate primer sequences; for each candidate primer sequence, calculating, using a processor, a plurality of candidate matches on the genome reference sequence for the candidate primer sequences; calculating, using the processor, verified matches on the genome reference sequence based on the candidate matching locations satisfying a plurality of matching verification rules; performing matching calculations of the verified matches to determine whether the verified matches form a match condition on the genome reference sequence; and generating a location profile on the genome reference sequence based on the match condition from the verified matches that meet a predetermined threshold.

18 Claims, 25 Drawing Sheets

- Amplified unintended regions are called off-targets
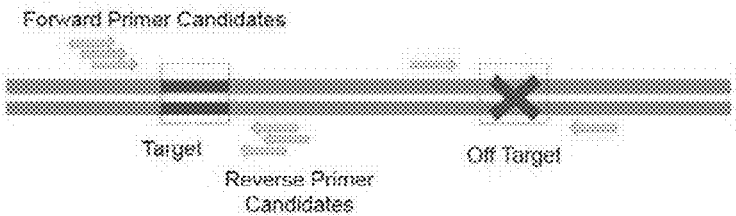
- With multiplex PCR primer design, primer sets for several targets have to be designed simultaneously
FIG. 14

2300

2400

US 10,971,249 B2

SYSTEMS AND METHODS FOR OFF-TARGET SEQUENCE DETECTION

CROSS-REFERENCE TO RELATED APPLICATIONS

This application claims priority to U.S. Provisional Patent Application No. 62/395,288, filed Sep. 15, 2016, which is hereby incorporated by reference herein in its entirety.

BACKGROUND

With multiplex PCR primer design, primer sets for several targets can be designed simultaneously. Primer pairs can target particular locations on a reference sequence (or reference string) representing positive and negative strands of a reference sequence such as a genome of nucleotides. But primers can amplify unintended regions of the genome (off-targets).

Off-target detection for candidate sequences (or candidate strings) can refer to identifying matching locations on a reference sequence and then determining whether any of such matching locations form an off-target match with another candidate sequence. Existing algorithms can rely on alignment tools, and indexing techniques can be used to speed up the process of detecting such off-target matching locations. However, such approaches do not scale well.

So, performance suffers due to the large number of candidate sequences and the sheer volume of computation involved, especially for large reference sequences in multiplex candidate primer sequence scenarios. Therefore, mere use of an index is unsuitable for application in real-world off-target detection scenarios.

There is therefore room for improvement.

SUMMARY

The Summary is provided to introduce a selection of concepts in a simplified form that are further described below in the Detailed Description. The Summary is not intended to identify key features or essential features of the claimed subject matter, nor is it intended to be used to limit the scope of the claimed subject matter.

A computer-implemented method of identifying off-target matches from a set of candidate primer sequences on a genome reference sequence can include: receiving onto a data storage unit a plurality of candidate primer sequences; for each candidate primer sequence, calculating using a processor a plurality of candidate matches on the genome reference sequence for the candidate primer sequences; calculating, using the processor, verified matches on the genome reference sequence based on the candidate matching locations satisfying a plurality of matching verification rules; performing matching calculations of the verified matches, using the processor, to determine whether the verified matches form a match condition on the genome reference sequence; and generating a location profile on the genome reference sequence based on the match condition from the verified matches that meet a predetermined threshold.

A computing system for identifying off-target matches from a set of candidate primer sequences on a genome reference sequence can include: at least one processor; and a memory storing instructions that, when executed by the at least one processor, causes the computing system to perform: receiving onto a data storage unit a plurality of candidate primer sequences; for each candidate primer sequence, calculating a plurality of candidate matches on the genome reference sequence for the candidate primer sequences; calculating verified matches on the genome reference sequence based on the candidate matching locations satisfying a plurality of matching verification rules; performing matching calculations of the verified matches to determine whether the verified matches form a match condition on the genome reference sequence; and generating a location profile on the genome reference sequence based on the match condition from the verified matches that meet a predetermined threshold.

A non-transitory computer-readable storage medium for identifying off-target matches from a set of candidate primer sequences on a genome reference sequence comprising computer-executable instructions that when executed cause a computing system to perform: receiving onto a data storage unit a plurality of candidate primer sequences; for each candidate primer sequence, calculating a plurality of candidate matches on the genome reference sequence for the candidate primer sequences; calculating verified matches on the genome reference sequence based on the candidate matching locations satisfying a plurality of matching verification rules; performing matching calculations of the verified matches to determine whether the verified matches form a match condition on the genome reference sequence; and generating a location profile on the genome reference sequence based on the match condition from the verified matches that meet a predetermined threshold.

As described herein, a variety of other features and advantages can be incorporated into the technologies as desired.

BRIEF DESCRIPTION OF THE DRAWINGS

FIG. 14 is a block diagram of example off-target match conditions.

DETAILED DESCRIPTION

Figure 1:
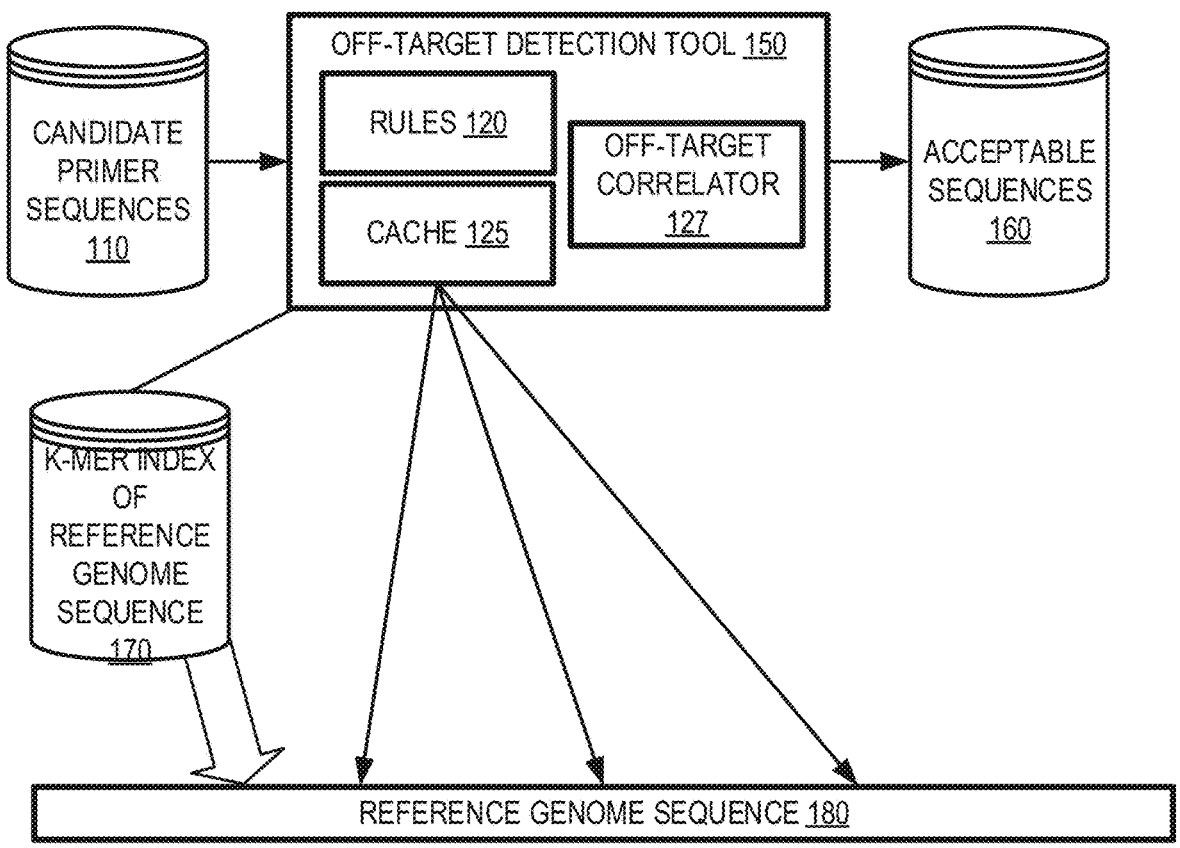
FIG. 1 is a block diagram of an example system implementing off-target matching detection for a reference sequence.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

DNA amplification is a technique that increases the number of copies of a target nucleic acid molecule (such as RNA or DNA). An example of DNA amplification is multiplex polymerase chain reaction (multiplex PCR). Multiplex PCR assays involve amplification of multiple target nucleic acid molecules in a single reaction. Typically, a pair of oligonucleotide primers is selected for amplification of each target nucleic acid molecule. A sample containing template nucleic acid comprising the target nucleic acid molecules is contacted with the selected pairs of oligonucleotide primers under conditions that allow for the hybridization of the pairs of primers to the targets on the template in the sample. The primers are extended under suitable conditions, dissociated from the template, re-annealed, extended, and dissociated to amplify the number of copies of the target nucleic acid molecules. The product of amplification can be characterized as needed, for example by nucleic acid sequencing.

The target nucleic acid molecules can be any nucleic acid molecule contained within the template nucleic acid in the sample. Target nucleic acid molecules for multiplex PCR assays can be 70-1000 base pairs in length, such as 100-150, 200-300, 400-500, and even 70-120 base pairs in length. The members of the primer pairs selected for the multiplex PCR assay hybridize to the up- and down-stream ends of the target nucleic acid molecule to initiate amplification.

Primers are nucleic acid molecules, usually DNA oligonucleotides of about 10-50 or 20-25 nucleotides in length (longer lengths are also possible). Primers can also be of a maximum length, for example no more than 25, 40, 50, 75 or 100 nucleotides in length. Hybridization specificity of a particular primer typically increases with its length. Thus, for example, a primer including 20 consecutive nucleotides typically will anneal to a target with a higher specificity than a corresponding primer of only 10 nucleotides. The 5' end of oligonucleotide primers for multiplex PCR assays can be linked to additional moieties (including additional oligonucleotides) for use in analysis of amplified target. For example, the 5' end of the primers in the primer pairs can be linked to additional oligonucleotide sequences that facilitate sequencing of the amplified target and analysis of resulting sequence reads (for example, adapter sequences, bar code sequences, and the like).

As discussed herein, design and selection of primers for multiplex PCR assays can include screening of a candidate primer having a candidate sequence to determine if there is a likelihood of an off-target hybridization event (off-target match) of the candidate primer to a template nucleic acid molecule having a reference sequence (reference string) that would interfere with the multiplex PCR assay. This involves identifying candidate hybridization locations (candidate matching locations) on the template nucleic acid molecule where the primer may hybridize, and determining if the candidate hybridization locations are verified hybridization locations (verified matching locations) based on a comparison of the candidate primer sequence with the sequence of the candidate matching locations according to one or more verification criteria (matching verification rules). In terms of the technologies described herein, candidate sequences can take the form of primer sequences, which are represented as paired primers (e.g., strings). For purposes of convenience, such internal representations are sometimes simply called a "sequence." An actual physical sequence is represented internally by a string of characters. The reference genome sequence can take the form of a representation of the reference genome or partial reference genome that is targeted by the primers. Thus, a reference genome sequence can represent a sequence of nucleotides and can indicate a designated 3' end and 5' end. Both positive and negative strands can be represented by a single reference genome sequence in a technique that generates reverse complements of the primers and includes them as candidate strings. A primer reverse complement that matches to the reference genome sequence indicates a match on the negative strand of the reference genome at the location indicated by the match. Such matches of primer reverse complements are of interest because if they are within a threshold distance (e.g., off-target condition window length), they can interfere with proper PCR reaction and result in an off-target condition.

Examples herein were performed using a representation of the human genome as the reference string for multiplex PCR reactions involving the human genome, but the technologies can be applied to genomes of other organisms. Still other implementations can use reference strings that represent sequences of proteins.

If a candidate hybridization location is identified as a verified hybridization location because the verification criteria are satisfied, then additional analysis can be performed to determine if hybridization of the candidate primer to the verified hybridization location, in combination with the hybridization of additional candidate primers for the multiplex PCR assay to corresponding verified hybridization locations on the template nucleic acid molecule, could interfere with the amplification of a target nucleic acid molecule and/or amplify of a non-target nucleic acid molecule (form an off-target condition). If the verification criteria for a first candidate primer would also apply to a second candidate primer (for example, because of similarity of the sequences of the two candidate primers), then for efficiency the analysis to determine if the verification criteria are satisfied for the first candidate primer can be reused for the second candidate primer.

In any of the examples herein, the technologies can be applied to specificity calculations for primers in a multiplex polymerase chain reaction scenario. Thus, fast specificity checking for multiplex polymerase chain reaction primer design can be accomplished. Multiplex polymerase chain reaction is widely used in diagnostic testing and forensic testing to simultaneously amplify multiple DNA regions of interest (targets). The successful running of a multiplex PCR largely depends on the design of a superior set of primer pairs. Each pair of primers comprises a forward primer and a reverse primer extracted from the upper and lower regions of the targets. Ideally, each designed pair should only amplify the intended targets, but not any unintended targets (off targets). The process of checking potential off-targets is called specificity checking, which is a key step in primer design.

Primer sequences can be grouped into clusters based on the target region of the reference genome sequence. For example, if a primer generation tool is used to generate primer candidates for multiple target regions in a multiplex PCR scenario, the primers can be stored as associated based on the target region (e.g., primers for different target regions are stored in different clusters). Common region determination can be performed as described herein based on such clusters.

Matching at the character level between a candidate primer sequence and a reference genome sequence can be calculated based on whether the two characters are complementary nucleotides (e.g., they would bind). Thus 'A' is considered complementary to 'T' and 'C' is considered complementary to 'G.'

Thus, the candidate primer sequences herein can be known to match a target, and it can be desirable that there be few or no off-target matches for such candidate primers. Candidate primer sequence pairs can be associated with known locations on the reference genome to represent their target and allow confirmation of an off-target condition. Matches at the target are considered to be on-target.

The task of specificity checking is nontrivial because there are several factors considered when deciding whether a DNA region could be amplified by a primer: notably, the overall similarity of the target and the stability of the 3' end. Typical existing approaches only report results with hundreds of primers at most. The techniques described herein can easily scale to hundreds of thousands of primers. Thus, the techniques can dramatically reduce the runtime of specificity checking by adopting rule calculation caching, off target prediction, and sequence proximity groupings.

Off-target detection can be implemented for a plurality of candidate primer sequences as described herein. Caching can re-use rule satisfaction calculations for candidate primer sequences sharing a common region. Match prediction can be used to filter candidates, and sequence proximity groupings can be used to facilitate identifying off-target match conditions. Other features relating to common region extension can be employed to achieve the technologies as described herein.

Benefits of the technologies include more scalability, especially for large numbers of candidate primer sequences targeting multiple regions on a large reference genome sequence.

Off-target detection can be useful in specificity calculations as described herein.

Therefore, overall performance of off-target detection can be enhanced as described herein.

Example 1—Example System Implementing Off-Target Matching Detection

FIG. 1 is a block diagram of an example system 100 implementing off-target matching detection for a reference genome sequence 180. In any of the examples herein, a string can take the form of a sequence of characters representing a string of values. Although called a "string" herein, internal representation can take the form of a string, array, or other data structure. Characters can take the form of characters or codes representing such characters.

Methods, computer systems and computer-readable media can comprise computer-executable instructions that when executed cause a computing system or processor to receive onto a data storage unit a plurality of candidate primer sequences. The candidate primer sequences can include at least one pair of primers to form a target (one on each side) in PCR.

For each candidate primer sequence, the processor or computer system can be caused to calculate a plurality of candidate matches on the genome reference sequence for the candidate primer sequences.

The processor or computer system can be caused to calculate verified matches on the genome reference sequence based on the candidate matching locations satisfying a plurality of matching verification rules. The candidate matching locations can be applied so that verified matches can include all amplifiable templates on the reference genome sequence for all pairs of candidates.

The processor or computer system can be caused to perform matching calculations of the verified matches to determine whether the verified matches form an off-target match condition on the genome reference sequence.

The processor or computer system can be caused to generate a location profile on the genome reference sequence based on the off-target match condition from the verified matches that meet a predetermined off-target threshold. The location profile can be a data structure, a class, an object, a value or a physical representation of the position on the reference genome sequence.

In the example, a plurality of candidate primer sequences 110 are received as input by the off-target detection tool 150. As described herein, such candidate primer sequences 110 can take the form of primer pairs targeting a particular location on a reference genome sequence 180 representing positive and negative strands of a reference genome as described herein. Therefore, the candidate primer sequences 110 are aimed at targets on the reference genome sequence 180. In some cases, off-target matches may also occur, whether in conjunction with a primer in the same pair or another pair (e.g., an inter-locus off-target match). In a multiplex scenario, the candidate primer sequences 110 can be targeted to multiple locations of the reference genome sequence 180, resulting in higher computational complexity when finding off-target matches. This higher computational complexity results in expending more resources and processing for a greater amount of time.

The off-target detection tool generates acceptable sequences 160 (e.g., input candidate primer sequences (e.g., pairs of primers) that are considered acceptable in light of detected off-target matches).

Internally, the off-target detection tool 150 can apply a plurality of rules 120 when determining whether a primer sequence matches a location of the reference genome sequence 180. The tool 150 can also make use of a k-mer index 170 of the reference genome sequence 180 to assist in matching determination. In practice, a match may initially be considered a candidate match and then verified to be a verified match.

A rule satisfaction calculation cache 125 can be used to alleviate the computational complexity associated with multiplex scenarios. As described herein, the cache 125 can leverage common regions in clusters of candidate primer sequences 110.

The off-target correlator 127 can accept verified matches and determine whether such verified matches result in an off-target match condition. As described herein, sequence proximity groupings can be applied to reduce computations involved in identifying an off-target match condition.

The off-target detection tool 150 can also accept settings as input that configure operation, such as parameters for the rules 120, or the like.

In any of the examples herein, although some of the subsystems are shown in a single box, in practice, they can be implemented as computing systems having more than one device. Boundaries between the components can be varied. For example, although the off-target detection tool 150 is shown as a single entity, it can be implemented by a plurality of devices across a plurality of locations. The rules 120 can be shared among multiple tools 150, and so forth.

In practice, the systems shown herein, such as system 100, can vary in complexity, with additional functionality, more complex components, and the like. For example, additional indexes, tables, and the like can be implemented as part of the system 100. Additional components can be included to implement security, redundancy, load balancing, auditing, and the like.

In practice, a large number of candidate primer sequences 110 and a large reference genome sequence 180 can be checked for off-target matches in a multiplex scenario.

The described computing systems can be networked via wired or wireless network connections. Alternatively, systems can be connected through an intranet connection (e.g., in a corporate environment, government environment, educational environment, research environment, or the like).

The system 100 and any of the other systems described herein can be implemented in conjunction with any of the hardware components described herein, such as the computing systems described below (e.g., processing units, memory, and the like). In any of the examples herein, the inputs, outputs, caches, indexes, strings, rules, and the like can be stored in one or more computer-readable storage media or computer-readable storage devices. The technologies described herein can be generic to the specifics of operating systems or hardware and can be applied in any variety of environments to take advantage of the described features.

Example 2—Example Method of Off-Target Matching Detection

Figure 2:
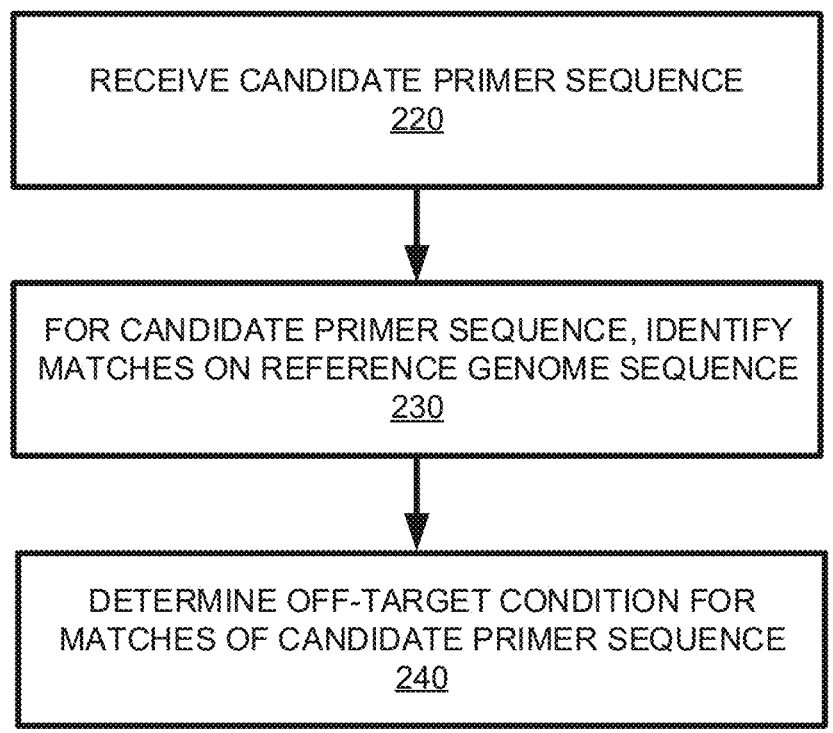
FIG. 2 is a flowchart of an example method of off-target matching detection.

FIG. 2 is a flowchart of an example method 200 of implementing off-target matching detection and can be implemented, for example, in a system such as that shown in FIG. 1. A plurality of candidate primer sequences targeting multiple targets on a reference genome sequence can be supported.

In practice, actions can be taken before the method begins, such as generating the candidate primer sequence pairs using a primer generation tool or the like.

At 220, a candidate primer sequence is received. The candidate primer sequence can take any of the forms described herein.

At 230, for a candidate primer sequence, matches on a reference genome sequence are identified. Match determination can involve applying a plurality of rules as described herein. For example, a plurality of candidate matching conditions can be identified on the reference genome sequence (e.g., via a matching rule as described herein). Out of the candidate matching locations, verified matching locations on the reference genome sequence can be identified. Such verification can comprise determining which of the candidate locations on the reference genome sequence satisfy matching rules as described herein.

Identifying candidate matching locations or verifying matching locations can comprise reusing a rule satisfaction calculation already calculated for another candidate primer sequence sharing a common region with the candidate primer sequence as described herein.

At 240, it is determined whether the verified matching locations form an off-target match condition on the reference genome sequence. As described herein, a match can be considered in conjunction with matches for another candidate primer sequence (e.g., on another, opposite direction reference genome sequence represented as described herein) to find a pair of candidate primer sequences that result in an off-target match.

Based on whether the verified matching locations form an off-target match condition, it is determined whether the candidate primer sequence is acceptable. For example, a threshold number of off-target matches can be applied, or no off-target matches may be allowed. Candidate reference sequences (or the associated candidate primer sequence pair) are included in the acceptable primer sequences if they meet the off-target threshold. More off-target matches result in lower specificity, making the candidate primer sequence less desirable.

As described herein, the method 200 can be performed for a plurality of candidate primer sequences (e.g., it is repeated for other candidate primer sequences). In practice, parallel and/or concurrent computation scenarios can be applied.

The method 200 and any of the other methods described herein can be performed by computer-executable instructions (e.g., causing a computing system to perform the method) stored in one or more computer-readable media (e.g., storage or other tangible media) or stored in one or more computer-readable storage devices. Such methods can be performed in software, firmware, hardware, or combinations thereof. Such methods can be performed at least in part by a computing system (e.g., one or more computing devices).

In any of the technologies described herein, the illustrated actions can be described from alternative perspectives while still implementing the technologies. For example, at 220, the method describes receiving a candidate primer sequence. However, such an act can also be described as "sending the candidate primer sequence" for a different perspective.

Example 3—Example Off-Target Matching Detection

In any of the examples herein, an off-target match can take the form of a pair of candidate primer sequences (e.g., whether from an original pair or two different pairs) that match at proximate locations as described herein. In practice, the proximate locations can be on two different (e.g., one original and one reversed and complementary to the original) reference genome sequences as described herein; computations can be accomplished with a single reference genome sequence by taking a reverse complement of a candidate primer sequence and including it in the candidate primer sequences. As described herein, detecting such an off-target match can be used to determine whether a candidate primer sequence is acceptable or not. A candidate primer sequence that exceeds an off-target match condition threshold (and its pair) can be considered unacceptable.

Example 4—Example k-Mers

In any of the examples herein, candidate primer sequences can be decomposed into substrings or subsequences of length k (the k-mers) to facilitate finding a match. The k-mers can be generated for a candidate primer sequence. In practice, all such substrings or subsequences are generated, but other arrangements are possible.

In any of the examples herein, identifying matching locations on a reference genome sequence for a candidate primer sequence can comprise decomposing the candidate primer sequence into k-mers and searching a k-mer index with the k-mers.

Example 5—Example Matching

In any of the examples herein, a sequence is considered to match a reference sequence at a particular location when rules are satisfied. Example matching rules can comprise the following:

Rule 1. There are at least k consecutive matching characters (e.g., matches at the character level).

Rule 2. There are not more than e*l character mismatches in total, where l is the length of the candidate primer sequence, and e is a parameter (e.g., a percentage, fraction, or the like).

Rule 3. There are not more than m character mismatches on an end of the candidate primer sequence.

Matching and mismatching characters can be determined based on complementary matches between characters as described herein. During match processing, a match can be treated as a candidate match until the three rules are verified as satisfied, at which point the match can become a verified match.

In any of the examples herein, the three matching rules above can be incorporated for determining matches. One or more rules can be designated as initial rules, while one or more others are designated as matching verification rules. For example, Rule #1 regarding consecutive matches can be designated as an initial rule, and candidate matches satisfying the initial rule can be verified via the other rules. Other arrangements for rules can be implemented.

In any of the examples herein, a match can take the form of the location on the reference genome sequence where the match occurs (e.g., an integer indicating i characters from the beginning of the reference genome sequence, a pointer to the location, or the like). The match can also take the form of an indication of the candidate primer sequence involved (and an identifier of a pair or an identifier of another candidate primer sequence in the pair). In scenarios with multiple reference genome sequences or representations thereof, the match can also indicate on which reference genome sequence the match occurs.

Verified matches can take the form of a match and also include an indication that the match has been verified. Verification can be implied (e.g., because the match appears in a list of verified matches).

Example 6—Example Candidate Match Verification

Figure 3:
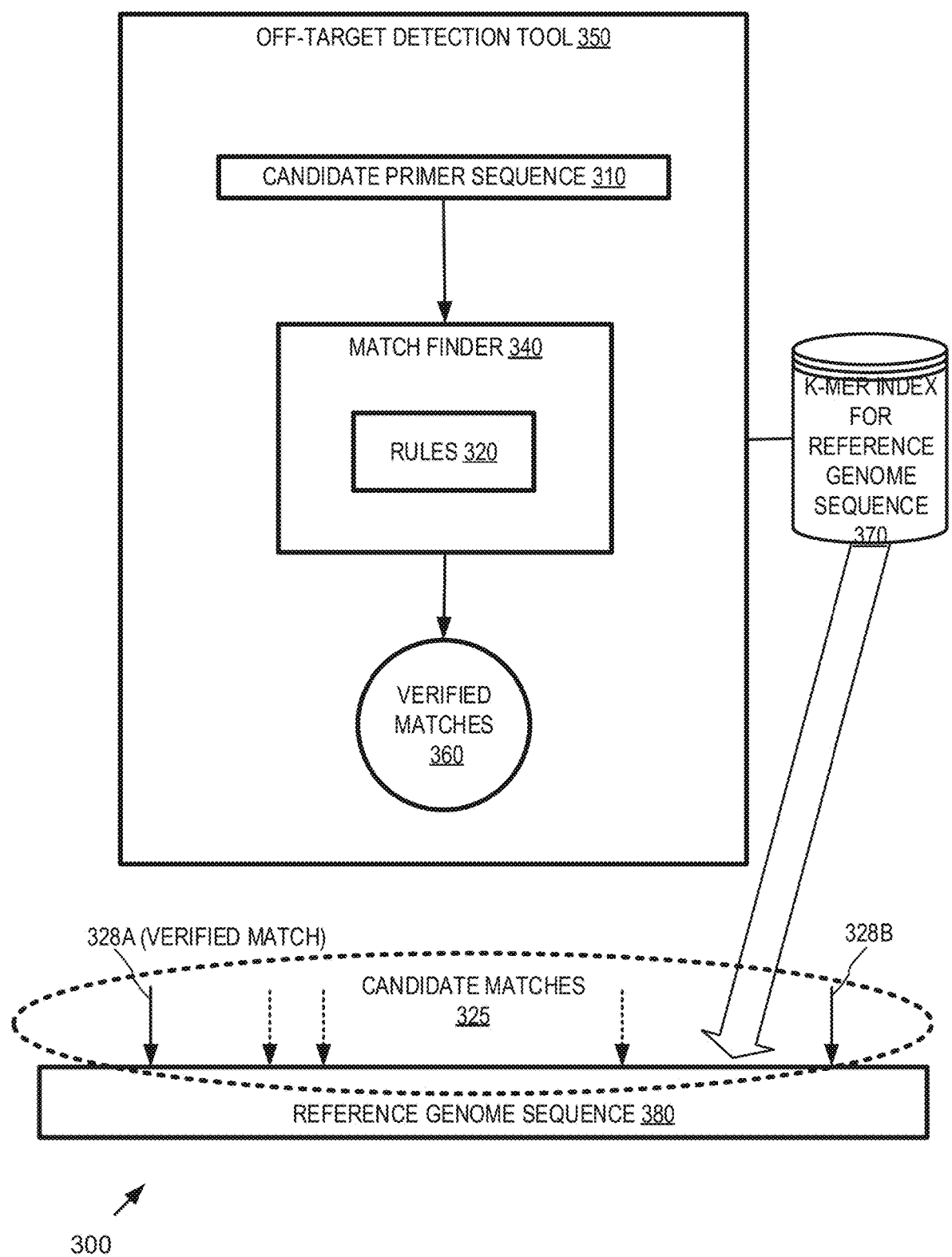
FIG. 3 is a block diagram of an example system verifying candidate matches.

In any of the examples herein, identifying matches on a reference genome sequence can take the form of verifying candidate matches. FIG. 3 is a block diagram of an example system 300 verifying candidate matches of candidate primer sequences 310 and can be used in any of the examples herein. By separating calculations for determining a match, some calculations can be re-used for candidate primer sequences sharing a common region. For example, certain candidate matches 325 can be safely skipped. Such an arrangement can be used to implement the system shown in FIG. 1.

In the example, an off-target detection tool 350 employs a match finder 340 that applies the matching rules 320 to determine verified matches 360.

In practice, a k-mer index 370 for the reference genome sequence 380 can be used to identify candidate matches 325 (e.g., the k-mer index of the reference genome sequence can be searched for decomposed k-mers of the candidate primer sequences, and a hit indicates a candidate match). Some of the matches 328A, 328B are verified as verified matches 360, while others are discarded from consideration.

Example 7—Example Method of Verifying Candidate Matches

Figure 4:
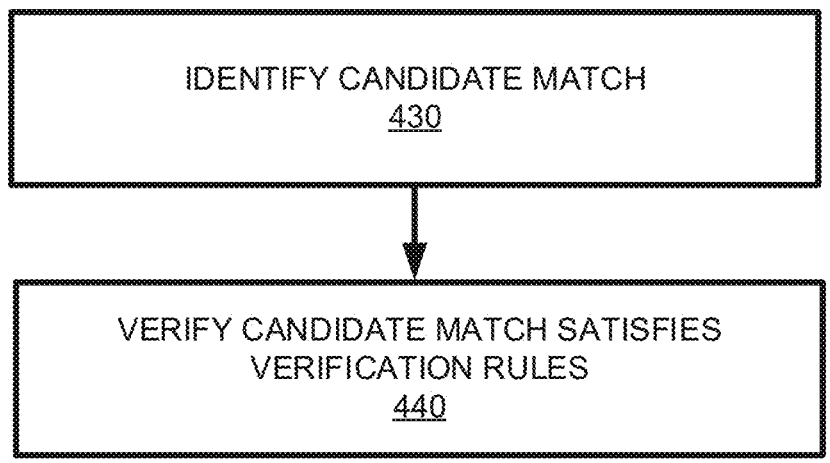
FIG. 4 is a flowchart of an example method of verifying candidate matches.

FIG. 4 is a flowchart of an example method 400 of verifying candidate matches and can be implemented, for example, in a system such as that shown in FIG. 3.

At 430, a candidate match (e.g., location on the reference genome sequence) can be identified (e.g., using the k-mer index to search for an occurrence of a k-mer of a candidate primer sequence to find if an initial matching rule such as Rule #1 described herein is satisfied or partially satisfied). The candidate match is then verified via the matching verification rules at 440. For example, the additional portions of the candidate primer sequence or further rules can be considered.

The method 400 can be performed for a plurality of candidate matches (e.g., the method is repeated for other candidate matches).

Example 8—Example Rule Calculation Cache for Common Regions

Figure 5:
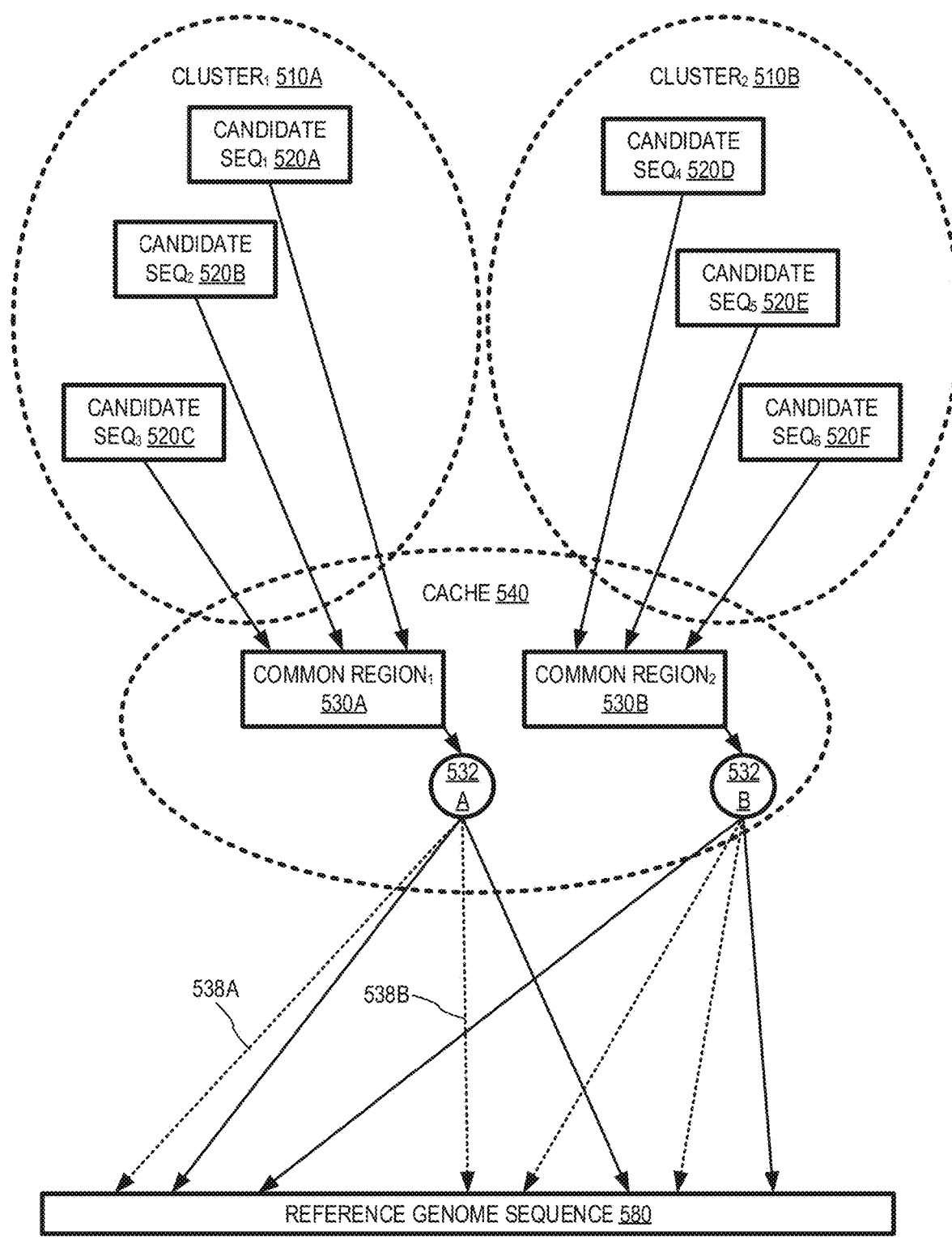
FIG. 5 is a block diagram of an example system having a cache for common regions within candidate primer sequences.

FIG. 5 is a block diagram of an example system 500 having a rule satisfaction calculation cache for common regions within candidate primer sequences that can be used in any of the examples described herein. In the example, clusters 510A, 510B or candidate primer sequences 520A-F are associated with common regions 530A-B, which are then associated with locations on the reference genome sequence 580.

The common regions 530A-B are regions (e.g., substrings, subsequences, or the like) of the candidate primer sequences that are shared among the candidates (e.g., the candidates contain identical substrings, subsequences, or the like).

The rule satisfaction calculation cache 540 is organized by the different common regions and stores rule satisfaction calculations 532A-B for respective of the common regions 530A-B that are associated with different respective clusters 510A-B of the input candidate primer sequences 520A-F. As described herein, certain candidate matches 538A, 538B can be safely skipped for the candidate primer sequences because a prior calculation has already determined that a matching rule was not satisfied (e.g., Rule #2 was not satisfied because there are too many mismatches).

Example 9—Example Rule Satisfaction Calculation Cache

In any of the examples herein, calculations for determining whether the rules are satisfied can be cached for use by a plurality of candidate primer sequences in a rule satisfaction calculation cache (e.g., a matching rule satisfaction calculation cache). As described herein, common regions among candidate primer sequences can be determined.

Based on the logic of the rules, certain calculations concerning rule satisfaction can be reused. For example, if it is known that a common region has at least k consecutive matches, any candidate primer sequence containing such a region satisfies rule #1 (e.g., in can only have k or more consecutive matches). Therefore, the determination that the region satisfies rule #1 can be reused for candidate primer sequences having the common region. Similarly, if it is known that a common region has more than e*1 mismatches, then any candidate primer sequence of length 1 will not satisfy rule #2 (e.g., it can have no more than e*1 mismatches). Therefore, the determination that the region does not satisfy rule #2 can be reused for candidate primer sequences having the common region.

Cached rule satisfaction calculations can include a stored location at which the calculation applies (e.g., a location on the reference genome sequence involved in the cached calculation, such as where a match occurs, where a mismatch occurs, or the like).

Multiple levels of the cache can store rule satisfaction calculations for different conditions or different lengths of sequences (e.g., 1, l+1, l+3, or the like).

In practice, non-common regions can then be incorporated into the determination. For example, if the cache indicates that there are m mismatches in the common region, further mismatches can be added to m to determine the overall candidate primer sequence mismatches and calculate if the overall mismatches meet rule #2.

Thus, total rule satisfaction calculations (e.g., whether the condition of a rule is satisfied) or partial rule satisfaction calculations (e.g., partial calculations of whether the condition of a rule is satisfied) can be cached.

Example 10—Example Method of Identifying Matches Via Cache

Figure 6:
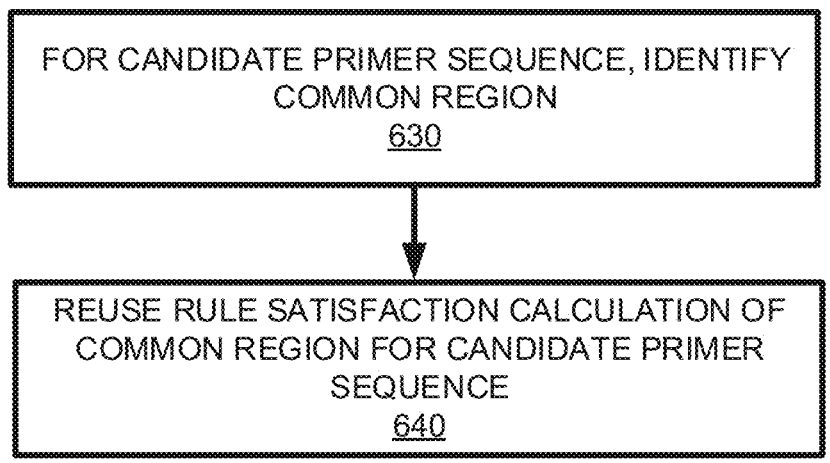
FIG. 6 is a flowchart of an example method of identifying matches for a candidate primer sequence via a cache.

FIG. 6 is a flowchart of an example method 600 of identifying matches for a candidate primer sequence via a cache and can be implemented, for example, in a system such as that shown in FIG. 5. In practice, such a method is typically performed by a match finder or other part of an off-target verification tool and can be performed as part of the method shown in FIG. 4.

A candidate primer sequence can be received when match processing begins.

At 630, a common region is identified for the candidate primer sequence. Associations between candidate primer sequences and common regions can be stored when the cache is built.

At 640, a rule satisfaction calculation of the common region is reused for the candidate match. In other words, the cache can be consulted instead of re-doing a calculation for rule satisfaction. For example, the calculation can be used to safely skip the candidate match (e.g., the candidate primer sequence cannot possibly match the location on the reference genome sequence.) Or, the calculation can be used to confirm that the candidate primer sequence meets a rule condition.

The method 600 can be done for a plurality of candidate primer sequences. So, it can be repeated for other candidate primer sequences.

Figure 7:
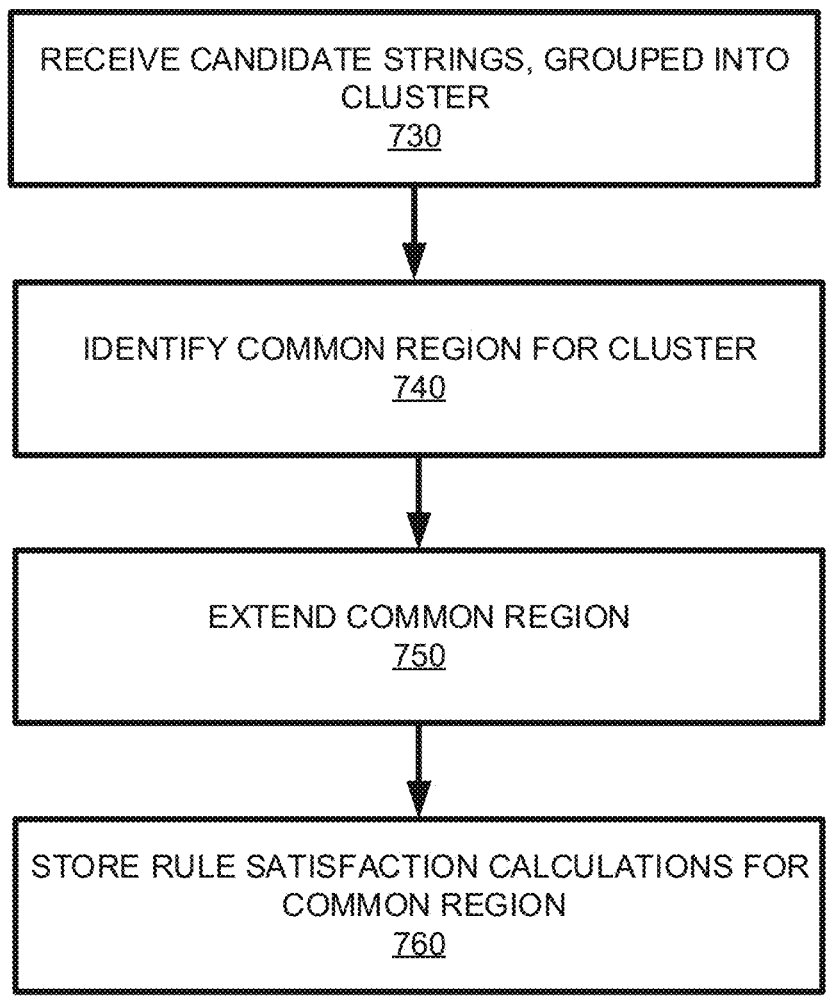
FIG. 7 is a flowchart of an example method of building a cache for candidate primer sequences.

Example 11—Example Method of Identifying Matches Via Rule Satisfaction Calculation Cache FIG. 7 is a flowchart of an example method 700 of building a cache for candidate primer sequences and can be implemented in any system employing a cache, such as that shown in FIG. 5. Cache building can be performed prior to or in conjunction with match processing (e.g., as shown in FIG. 4).

At 730, candidate primer sequences grouped into a cluster are received. In practice, it may be known that a set of candidate primer sequences are associated with a common origin, and they can be grouped into a cluster accordingly. Or, clustering can be performed by finding likely common regions among the sequences.

At 740, a common region is identified for the cluster. An incoming cluster may already have some initial indication of a common region or likely common region, or the candidate primer sequences can be aligned to determine a common region. The initial common region can be called a "seed" before it is extended.

In any of the examples herein, the common region can be extended as shown at 750. Computing resource increases can be balanced against computing resource decreases as a result of extending the common region. The advantages and disadvantages of extending the common region can be considered when determining whether to extend the region. For example, a computing resource increase for extending the region (e.g., the resources expended for building the cache) can be calculated, the computing resource decrease for extending the common region (e.g., the resources saved by searching with the cache) can be calculated, and the computing resource increase for not extending the region (e.g., the resources expended for searching without the cache) can be calculated. Deciding whether to extend the common region can be determined by balancing the computing resource increases against the computing resource decrease. For example, extending the common region may only reach a subset of candidate primer sequences in the cluster.

At 760, rule satisfaction calculations for the common region are stored as described herein. Such calculations can be associated with the common region in the cache for later use when processing candidate primer sequences having the common region. Similarly, associations between the common region and candidate primer sequences containing the common region can be stored.

The method 700 can be performed for a plurality of clusters. For example, it can be repeated for other clusters.

In any of the examples herein, the common region between a candidate primer sequence and another candidate primer sequence can be identified. A rule satisfaction calculation can be performed for the common region, and the rule satisfaction calculation can be stored in a cache. Based on the cache, the calculation can be skipped (e.g., for the candidate primer sequence). The cache can support multiple levels (e.g., for respective different lengths of candidate primer sequences) as described herein.

Example 12—Example System Implementing Multi-Level Cache

Figure 8:
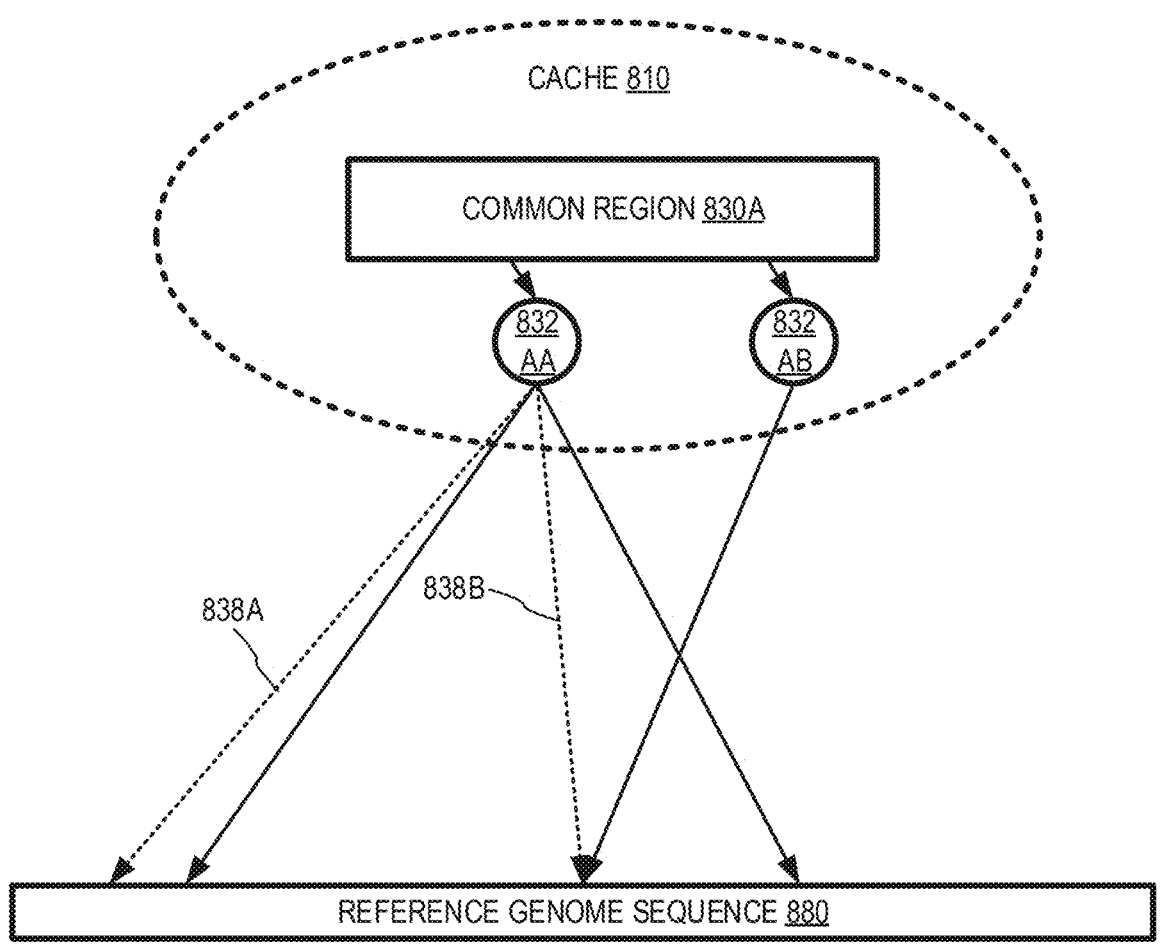
FIG. 8 is a block diagram of an example system implementing a multi-level cache.

FIG. 8 is a block diagram of an example system 800 implementing a multi-level cache 810 and can be implemented in any of the examples herein using a cache.

In the example, the rule satisfaction calculation cache 810 is organized by common region 830A and includes separate rule satisfaction calculations 832AA and 832AB that are stored for different levels of the cache 810.

For example, calculations for different rules, or calculations for different parameters of the rules (e.g., different candidate primer sequence lengths) can be stored.

Various candidate matches for the common region and the reference genome sequence 880 can be associated with the cache. Certain candidate matches 838A, 838B can be indicated as not meeting a rule and therefore can be safely skipped when processing other candidate primer sequences containing the common region. Those candidate primer sequences of different lengths can limit re-use of calculations to those appropriate for the rule (e.g., Rule #2 above incorporates a length component).

Example 13—Example System Implementing k-Mer Index

Figure 9:
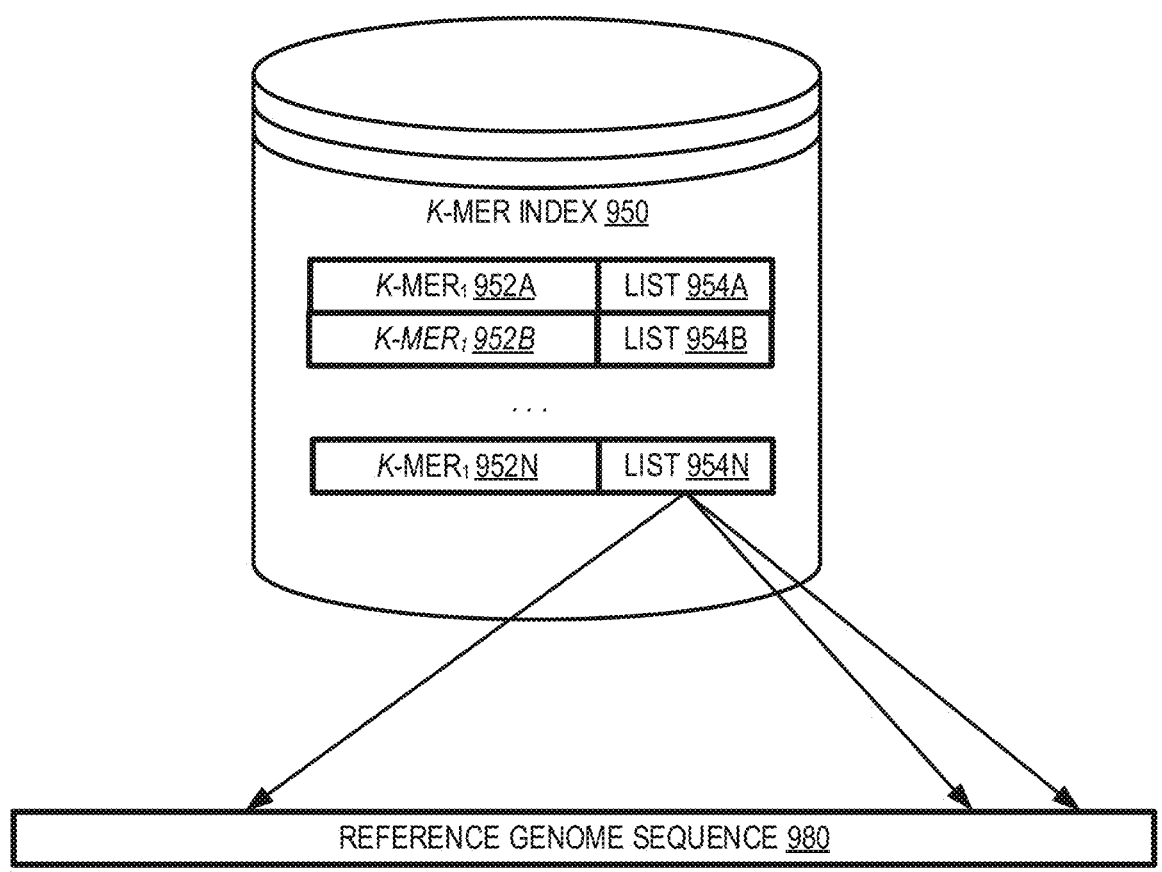
FIG. 9 is a block diagram of an example system using a k-mer index.

FIG. 9 is a block diagram of an example system 900 implementing a k-mer index 950. The example shows a basic implementation. In practice, any number of variations are possible. Any variety of k-mer index schemes can be employed for the technologies.

In the example, the index 950 comprises k-mer keys 952A-N and respective locations 954A-N at which the k-mer occurs in the reference genome sequence 980. The locations can take the form of a list (e.g., of integers, pointers, or the like that specify a location in the reference genome sequence 980).

Example 14—Example Off-Target Predictor

In an implementation checking specificity of primers, off-target determination can be done with reference to whether the primers would amplify unintended regions of the genome. FIG. 14 is a block diagram of example off-target match conditions.

When unintended regions are amplified, an off-target match condition exists for the primers. A primer pair can comprise a forward primer and a reverse primer. When a primer pair binds at an unintended location, unintended amplification can result. Thus, detection of a match of one primer at a location on one strand of the genome in conjunction with detection of a match of another primer at a neighboring location on the other strand of the genome indicates an off-target match condition. When the primer is from another pair, an off-target match condition still results and is called an "inter locus off target" condition. With multiplex PCR primer design, primer sets for several targets are designed simultaneously, making primer selection more complex and challenging.

A method of detecting off-targets can receive collected matches (e.g., matching locations for primers meeting the rule conditions) on the reference genome sequence and check if there are matches within a threshold distance (e.g., off-target condition window length) of each other on the reference genome sequence. Such a method can perform determining whether verified matching locations form an off-target match condition on a reference genome sequence when considered in conjunction with at least one other match for at least one other candidate primer sequence. Reverse complements of primers can be included as described to account for the negative strand. Such collected matches that are not at a desired target location on the reference genome sequence are considered an off-target match. One method of detecting off-target conditions can simply compare each match location to the other match locations (e.g., each other match location) to see if they are within the threshold distance, resulting in a computation of order $n^2$. Upon detection of two match locations within a threshold distance, further processing can be done (e.g., to confirm that the matches are on different strands of the reference genome sequence) to confirm the off-target condition. The strand of a match can be stored as part of its representation (e.g., if the associated candidate primer is a reverse complement, then it is indicated to be a match on the negative strand; otherwise, it is a match on the positive strand). A set of matches at an intended target is not indicated as an off-target condition.

In any of the examples herein, the off-target condition window length can be equal to or substantially similar to that of the maximum expected length of the target nucleic acid molecules (e.g., typically 25-1000 base pairs in length, 200-1000, 500-1000, 200-800, or 300-700 base pairs in length) in a PCR reaction as described herein. A value of 1000 was used for the off-target condition window length in examples described herein, off-targets being scored based on their length.

Figure 10:
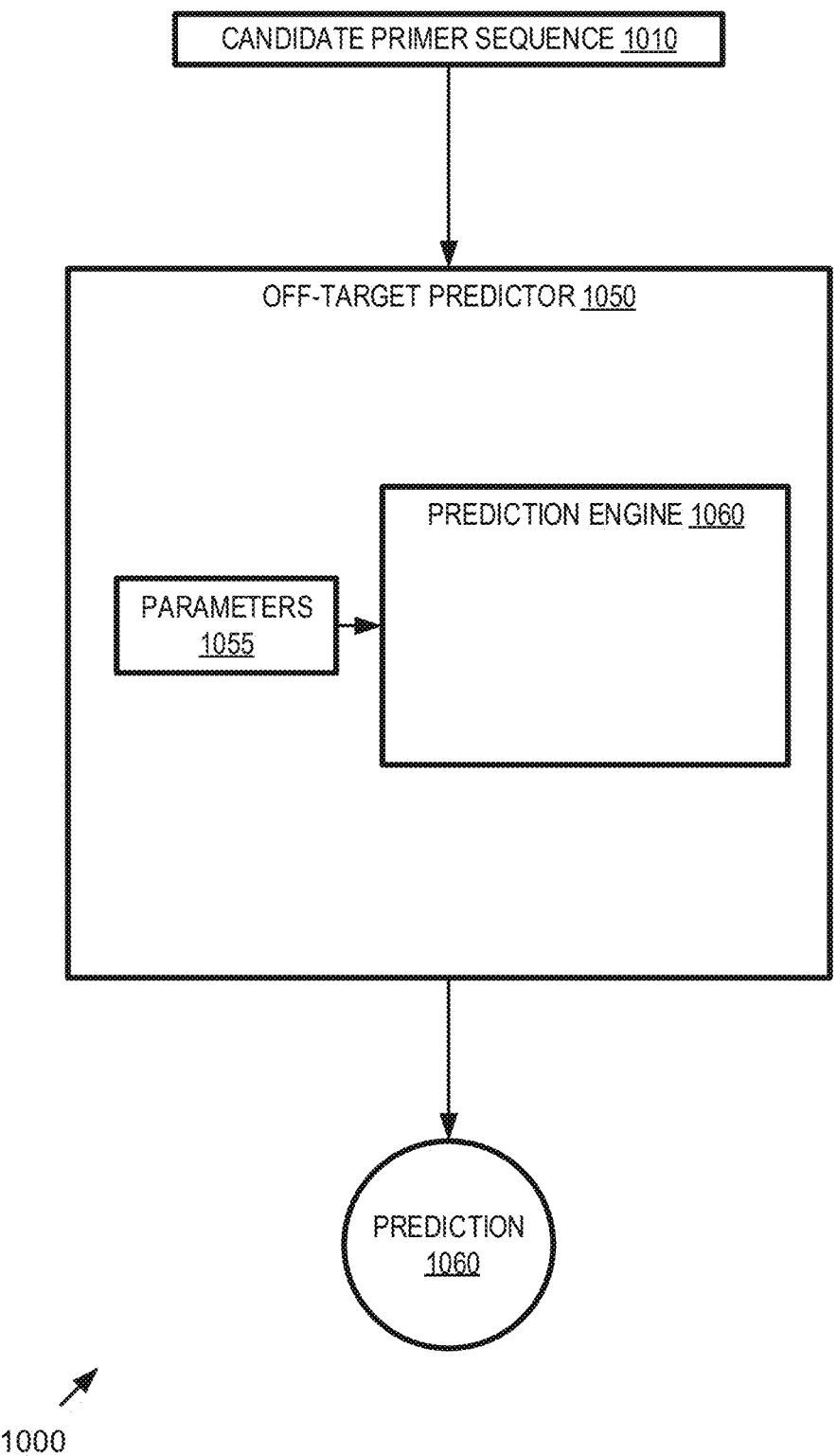
FIG. 10 is a block diagram of an example system implementing an off-target predictor.

FIG. 10 is a block diagram of an example system 1000 implementing an off-target predictor and can be used in any of the examples herein for a candidate primer sequence. Such a predictor can be used with implementations having or not having a cache. Before searching for matches, a number of matches can be predicted. A large number of matches is correlated with an off-target match. So, if the predicted number of matches meets a threshold, the candidate primer sequence can be discarded (e.g., skipped), thereby reducing the number of calculations and increasing performance.

One predictor takes the form of the following Calculation A using trained parameters a, b, c, and d:

$$y = e^{(a*\log x + b*l + c*\text{floor}[l*e] + d)}$$

where y: number of hits (+ or − strand, which are highly correlated)

x: number of candidate hits (matches) returned by k-mer index for candidate primer sequence l: length of the candidate primer sequence e: fraction of mismatches allowed (from rule #2) or the mismatch rate allowed or the error rate allowed.

The parameters a, b, c, and d can be calculated from historical data. Linear regression can be used to fit the predictive model Calculation A to the observed data set of y and x hits. The parameters a, b, c, and d can be applied if an additional value of x is then given without its accompanying value of y, and the fitted model can be used to make a prediction of the value of y.

In the example, the off-target predictor 1050 accepts a candidate primer sequence 1010 as input and applies the parameters a, b, c, and d to a prediction engine 1060 (the calculation shown above) to generate a predicted number of matches on the reference genome sequence. l and x can be derived from the candidate primer sequence 1010. If the matches meet (or exceed) a threshold, the candidate primer sequence can be discarded from consideration (e.g., matching processing need not be performed for the candidate primer sequence or its paired sequence). Thus, the off-target detection tool can store the threshold and apply it as described.

In any of the examples herein, the off-target prediction technologies can be used as a pre-filter to discard those candidate primers having more than a threshold number of hits. In one implementation involving the human genome, a threshold (e.g., off-target condition window length) of 1,000 was used, but other values in the range of 800-1200 (e.g., 900, 1100, or the like can be used). A prediction is generated for candidate primers as described herein, and if the number of predicted hits meets the threshold, the candidate primer is discarded from consideration (e.g., the cache need not be considered for the candidate primer sequence).

Figure 23:
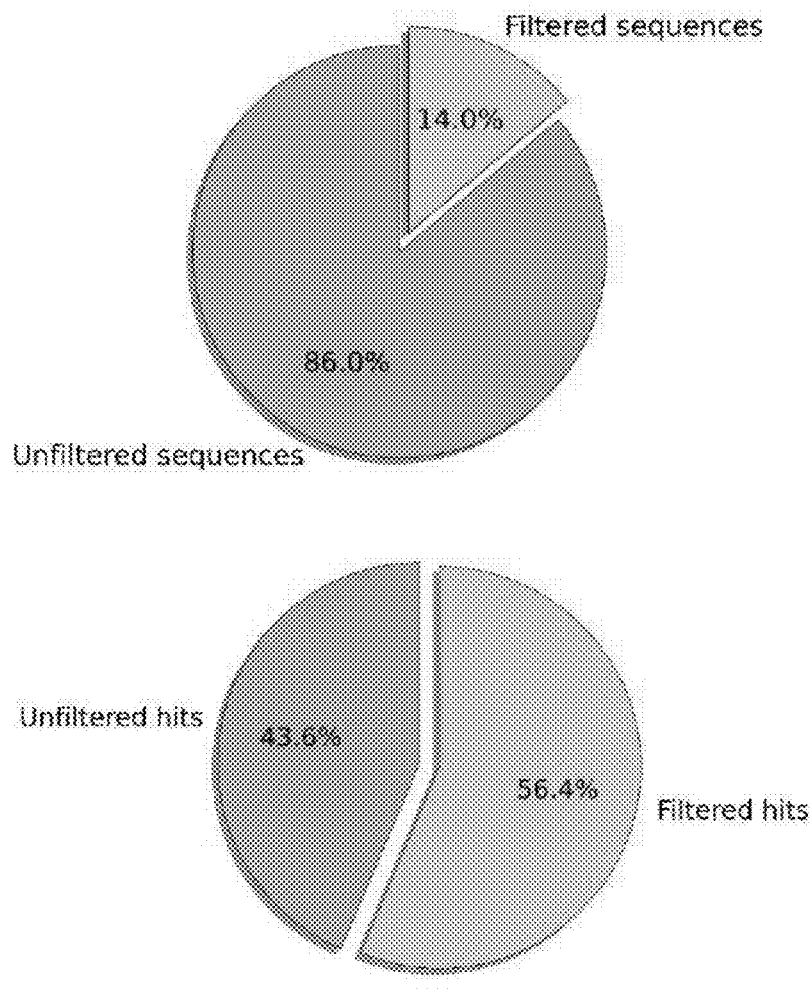
FIGS. 23 and 24 show results for applying match prediction before searching for matches.

FIG. 23 depicts a block diagram showing results for applying match prediction via Calculation A described above, with the parameters, before searching for matches. In the example, a threshold of 1000 matches was set. If the prediction for a particular candidate primer sequence met the threshold, it was discarded from consideration. Runtime improvement and dramatic reduction of memory usage resulted. The off targets checking time was reduced from 1 hour to 10 minutes. The straightforward method resulted in 5.5 seconds per primer; the cached method resulted in 0.38 seconds per primer; the prediction/filtering method resulted in 0.29 seconds per primer. By filtering 14% of the sequences, 56.4% of the matches (hits) were filtered. Filtering sequences with too many hits can reduce memory usage.

Figure 24:
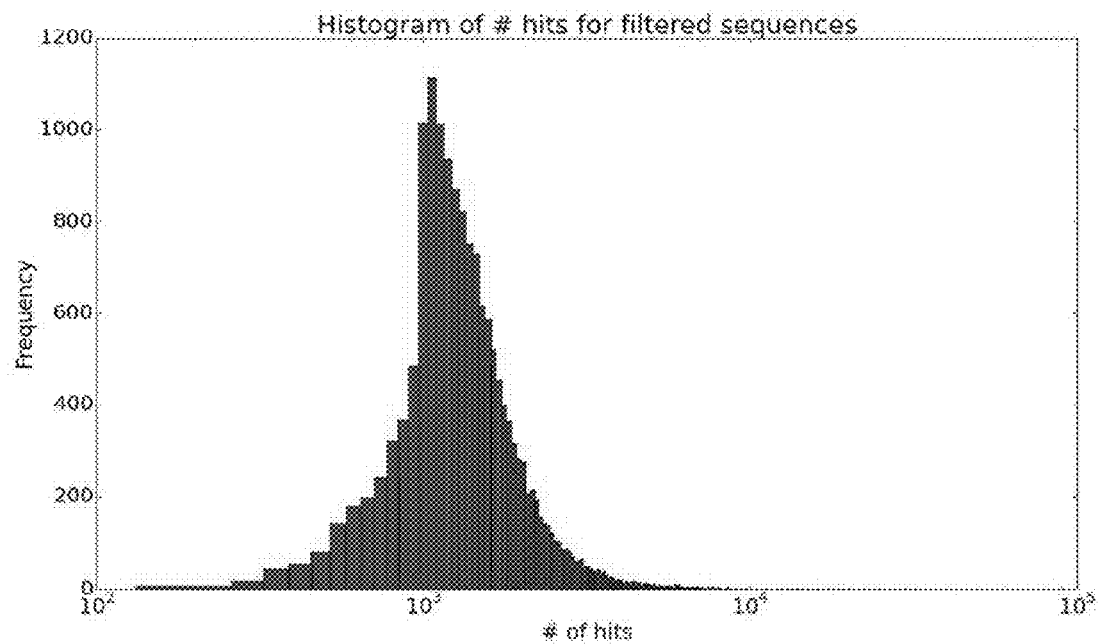

As shown in FIG. 24, more than 93% of the filtered sequences have more than 800 actual observed hits. Therefore, filtering based on the prediction generated by Calculation A can be considered valid.

Other thresholds of about 250, about 500, about 1000, about 1500, or about 2000 could also be used.

Thus, filtering of some candidate primer sequences can be accomplished by removing primer sequences that are predicted to have many hits (e.g., and thus are likely to result in an off-target match condition). The embodiments of FIGS. 10 and 11 can implement such an approach. Thus, in any of the examples herein, primers can be pre-filtered by removing those primers that are predicted to have a threshold number of hits (matches). Such a prediction can be generated by training a calculated result based on observations of actual matches (e.g., as it varies based on length of the primer). Any number of calculations generating a prediction can be used. The following Calculation A can be used as an example with parameters as described herein:

$$y = e^{(a*\log x + b*l + c*floor[l*e] + d)}$$

Any of the following embodiments can be implemented. For example, pre-filtering of candidate primers can be achieved using the match prediction technologies of FIGS. 10 and 11 in any multiplex PCR scenario, independent of the cache and sequence proximity groupings technologies. So, for a candidate primer sequence considered for inclusion as a primer in a multiplex PCR reaction, the sequence can be received, a prediction of a number of matches on the reference genome sequence for the candidate primer sequence can be generated, and responsive to determining that the predicted number of matches exceeds a threshold, the candidate primer sequence can be discarded from consideration (e.g., filtered out). The calculation and thresholds can take the forms described herein.

Off-target detection via sequence proximity groupings can be applied in any multiplex PCR primer specificity evaluation scenario, independent of the cache and match prediction technologies. So, for a plurality of verified matches for a plurality of candidate primers, the verified matches can be placed into sequence proximity groupings as described herein. Such matches can be verified via techniques other than the cache techniques described herein (e.g., by applying matching rules without the cache described herein). The proximity groupings can then be checked to identify an off-target match condition.

Example 15—Example Method of Off-Target Prediction

Figure 11:
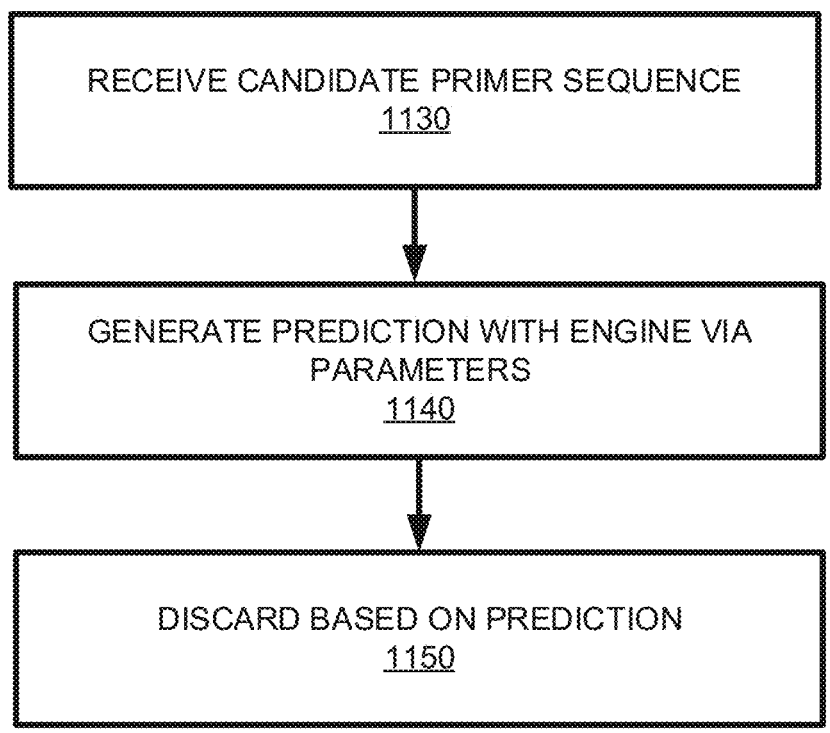
FIG. 11 is a flowchart of an example method of generating an off-target prediction for a candidate primer sequence.

FIG. 11 is a flowchart of an example method 1100 of generating an off-target prediction for a candidate primer sequence and can be implemented, for example, in a system such as that shown in FIG. 10. Such a method can be used with implementations using or not using a cache.

At 1130 a candidate primer sequence is received.

At 1140, a prediction of the number of matches on the reference genome sequence is generated via applying the parameters to a prediction engine.

At 1150, the candidate primer sequence is discarded from consideration (e.g., the actual matches are not determined) responsive to determining that the predicted number of matches exceeds a threshold.

In practice, the method 1100 can be performed for a plurality of candidate primer sequences (e.g., it is repeated for other candidate primer sequences).

Example 16—Example System Implementing Proximity Groupings

Figure 12:
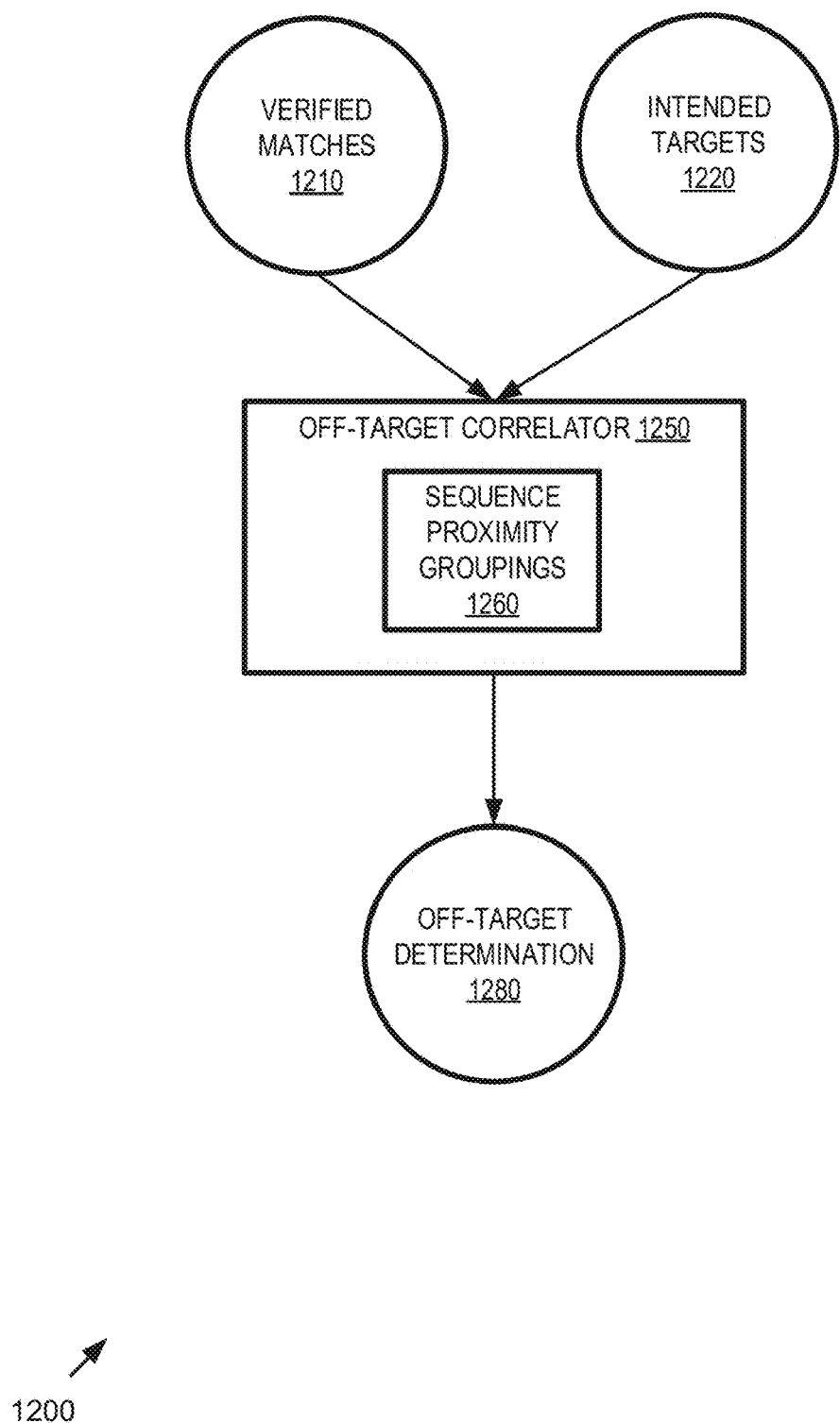
FIG. 12 is a block diagram of an example system implementing sequence proximity groupings.

FIG. 12 is a block diagram of an example system 1200 implementing string or sequence proximity groupings and can be used in any of the examples herein to identify an off-target match condition. The off-target correlator 1250 can be incorporated into an off-target detection tool (e.g., as correlator 127 in tool 150 of FIG. 1). Sequence proximity groupings can be used in systems not having a cache.

The correlator 1250 accepts verified matches 1210 and intended targets 1220. In practice, the system can process verified matches 1210 for a large number of candidate primer sequences determined via any of the technologies described herein. The intended targets 1220 indicate the targets intended for the candidate primer sequences, which can be organized in pairs as described herein.

The correlator 1250 can create sequence proximity groupings 1260 that assist in determining whether a verified match for a candidate primer sequence is an off-target match. As described herein, such a determination can be made with reference to two reference genome sequences for which processing has been performed; two sequences can be represented via a single sequence as described herein.

Based on the sequence proximity groupings 1260, the correlator 1250 can output an off-target determination 1280. Such a determination can indicate that a particular candidate primer sequence results in an off-target match. Other information such as where on the reference genome sequence the off-target match occurs, whether it is an inter-locus off-target match, or the like can be included.

Figure 13:
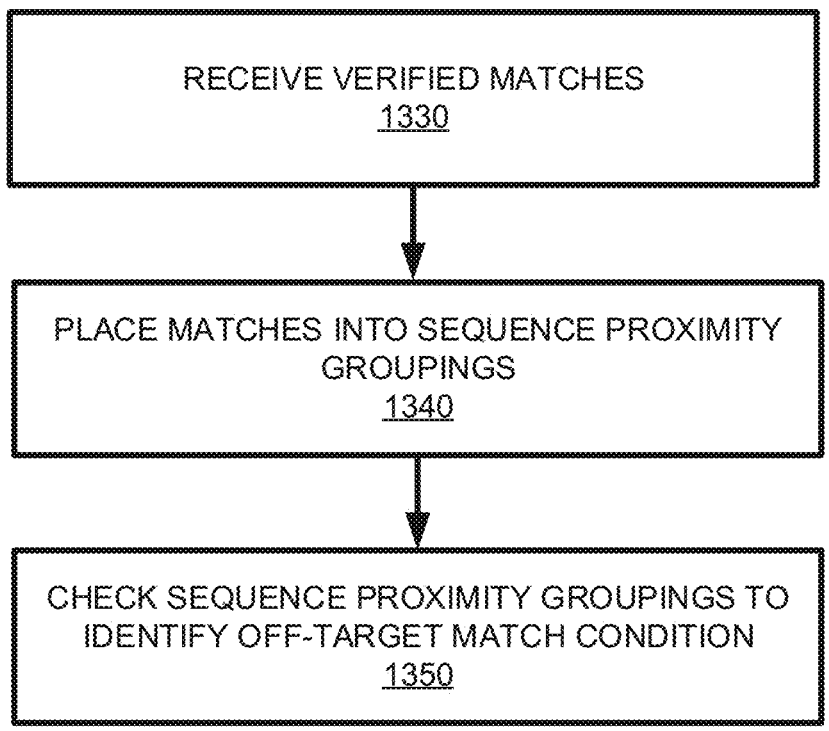
FIG. 13 is a flowchart of an example method of identifying off-target matches via sequence proximity groupings.

Example 17—Example Method of Identifying Off-Target Match Condition Via Proximity Groupings FIG. 13 is a flowchart of an example method 1300 of identifying off-target matches via sequence proximity groupings and can be implemented, for example, in a system such as that shown in FIG. 12 (e.g., by an off-target correlator). Sequence proximity groupings can be used in methods using or not using a cache.

At 1330, a plurality of verified matches for a plurality of candidate primer sequences are received. As described herein, a verified match can include an indication of where on the reference genome sequence the match occurs.

At 1340, the matches are placed or clustered into sequence proximity groupings according to where on the genome sequence the matches occur. The groupings can be based on an off-target condition window length.

At 1350, the sequence proximity groupings can be checked to identify an off-target match condition as described herein.

Example 18—Example Sequence Proximity Groupings

In any of the examples herein, a reference genome sequence can be divided into ranges of locations. The size of the ranges can be based on an off-target condition window length. Thus, a first group covers locations 1 through window_length, a second group covers locations window_length+1 through window_length*2, etc. The range for a group g is thus 1+(window_length*(g−1)) through (window_length*g).

The group contains a list of the verified matches that occur at a location within the range of the group. Checking for an off-target match pair can be simplified because checking need only be done between match pairs occurring in proximate locations (e.g., neighboring groups) of a reference sequence. In this way, matches within an off-target condition window_length's distance of each other can be identified and processed for detecting an off-target condition.

Example 19—Example Implementation: Specificity Calculations for Primer Pairs

As described herein, a k-mer index can be applied, and intermediate results can be cached in the rule satisfaction calculation cache to reduce runtime without losing accuracy.

The task of specificity checking can proceed via two phases: searching primer hits (matches) and checking whether such matches result in an off-target match condition for two of the primers. Given a primer p with length l and a genome region r, r is a hit of the primer when it satisfies the following three conditions (matching rules): 1. There are at least k consecutive matches 2. there cannot be more then e*l mismatches in total and 3. There cannot be more than m mismatches on the 3' end of the primer. The conditions can be implemented as the matching rules as described herein.

```
GCAGCTGGTTGTGATCACGT
||||||||||xx||||x|x
GCAGCTGGTTTGGATCAGGG
```

For example, genome region r can be a hit when: 1. there are at least 6-10 (such as at least 6-8) consecutive matches, for example, at least 6, 7, 8, 9, or 10 consecutive matches, between the primer nucleotide sequence and the nucleotide sequence of genome region r, 2. no more than 20% (such as no more than 15% or no more than 10%) of the primer nucleotides are mismatched between the primer nucleotide sequence and the nucleotide sequence of genome region r, and 3. No more than 5 mismatches (such as no more than 4, no more than 3, or no more than 2 mismatches, or no more than 1 mismatch) between the primer nucleotide sequence and the nucleotide sequence of genome region r are present (e.g., consecutively) on 20% of the primer (by nucleotides) from the 3' end of the primer. The 3' end of the primer can be defined as 5 base pairs long in some embodiments. In other embodiments, the 3' end of the primer can be defined as 1-5 base pairs long. For example, the cutoff can be no more than 3 mismatches in the last 5 base pairs or no more than 2 mismatches in the last three base pairs. dependent on the polymerase than the length of the primer. Typically, a 3' end mismatch could prevent amplification (the polymerase may not be able to extend from a mismatch). However, high-fidelity polymerases typically can chew back mismatching bases and resynthesize, thus correcting errors, but also increasing the chance an off-target is amplified.

Thus, the technologies allow specification of the total number of mismatches allowed as a percentage of the primer length between primer and targets. A custom region at the 3' can be defined, and the number of mismatches allowed in the region between the primer and targets can be specified. Specificities for multiple pre-existing primers can be determined. The technologies can scale to hundreds of thousands of primers.

Matches on the reference genome strands can be considered candidate matches until the three Rules are verified as satisfied.

Example 20—Example Implementation: Off-Target Determination

Figure 15:
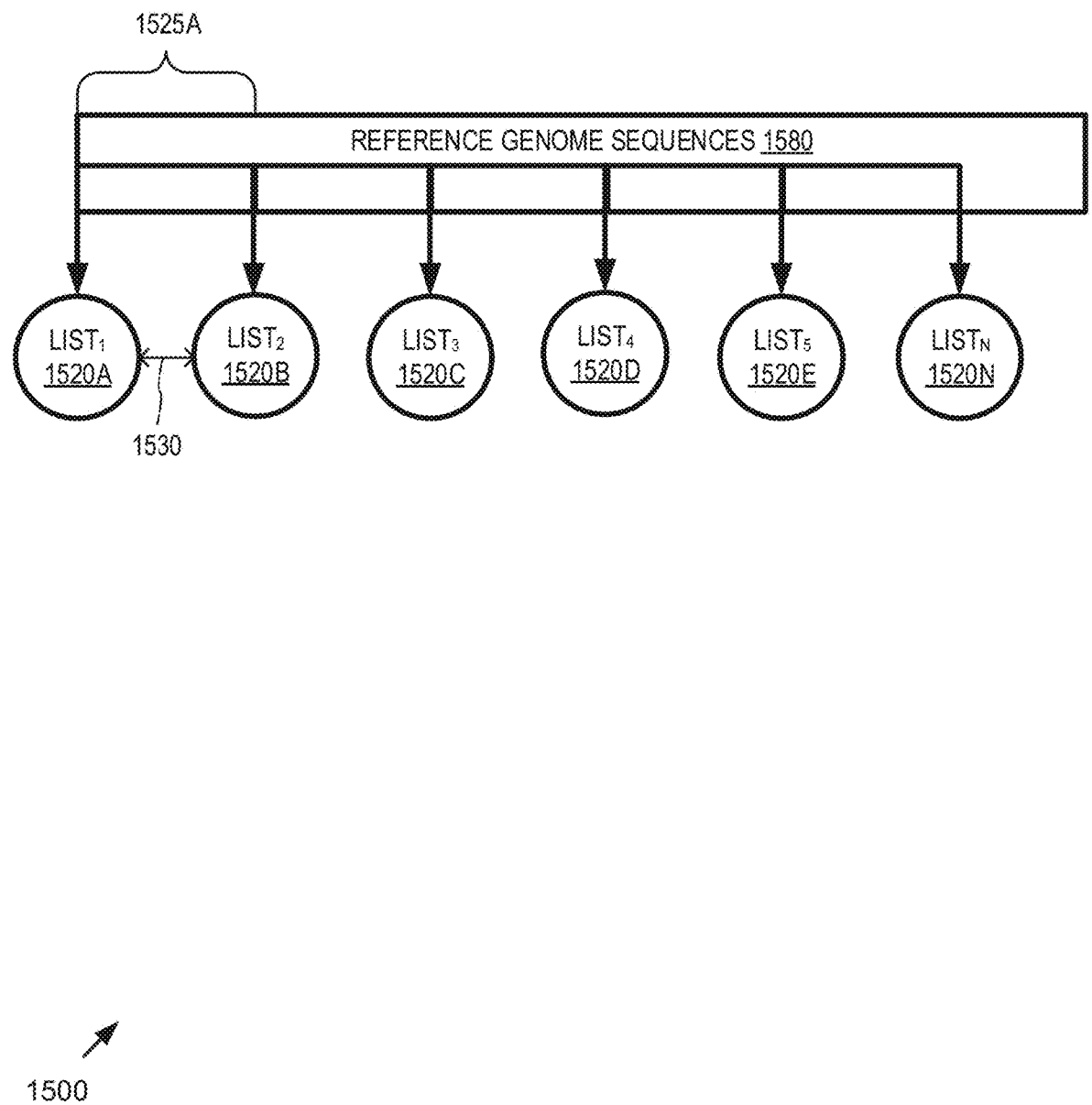
FIG. 15 is a block diagram of an example system employing sequence proximity groupings for off-target determination.

FIG. 15 is a block diagram of an example system 1500 employing sequence proximity groupings for off-target determination and can be used for the arrangements shown in FIG. 12 or 13. In the example, the target sequence strands 1580 for the reference genome sequence are represented by a single reference genome sequence divided into ranges according to an off-target condition window length 1525A. The negative strand is represented by the reference genome sequence 1580 in that the reverse complement of a primer is also included as a candidate primer sequence. Thus, off-target locations that would cause undesirable amplification or interference with amplification of target locations during the PCR process can be identified. In this way, sequence proximity groupings as described herein are implemented. In an alternative embodiment, two different sequences (reversed and complementary to each other) can be used to represent the different strands.

Verified matches against the strands 1580 are placed in lists 1520A-N according to where on the strand the verified match occurs. For example, the method of FIG. 2 can be performed for the primer sequences and the reverse complements of the primer sequences, resulting in verified matches for both strands. Off-target matches can then be identified using the lists.

Checking for off-target match conditions can be accomplished by checking 1530 matches within a same group and in neighboring groups. Because checking can proceed seriatim for the groups, in practice, a group can simply be checked against the next group (e.g., when processing the list 1520B, it is not necessary to check against list 1520A because processing for 1520A has already done so). For example, matches in the list 1520A can be checked against matches in the list 1520B to see if an off-target match condition exists (e.g., there are two primer hits within an off-target condition window length of each other that are not a desired target), and then matches in 1520B can be checked against 1520C and so forth. If so, the primer in the off-target match condition can be noted as involved in an off-target match condition. The primer pair can also be so noted.

The lists 1520A-N thus can function as an index of the matches to greatly speed up off-target detection processing.

Specificity can thus be calculated based on the number of off-target match conditions detected per primer or primer pair. Specificity can take the form of a counted number of off-target matches. Some applications may demand that a single off-target match is considered unacceptable. However, more complex statistical techniques can be applied depending on the application because it may not always be possible to find candidate primers that satisfy such stringent conditions.

Off-target prediction can be accomplished, where a candidate string takes the form of a candidate primer sequence. Such candidate primer sequences can be pre-filtered from further consideration when the prediction meets a threshold as described herein. For such pre-filtered sequences, the cache and off-target consideration calculations need not be performed. Such calculations can instead be skipped.

Example 21—Example Further Description

Figure 16:
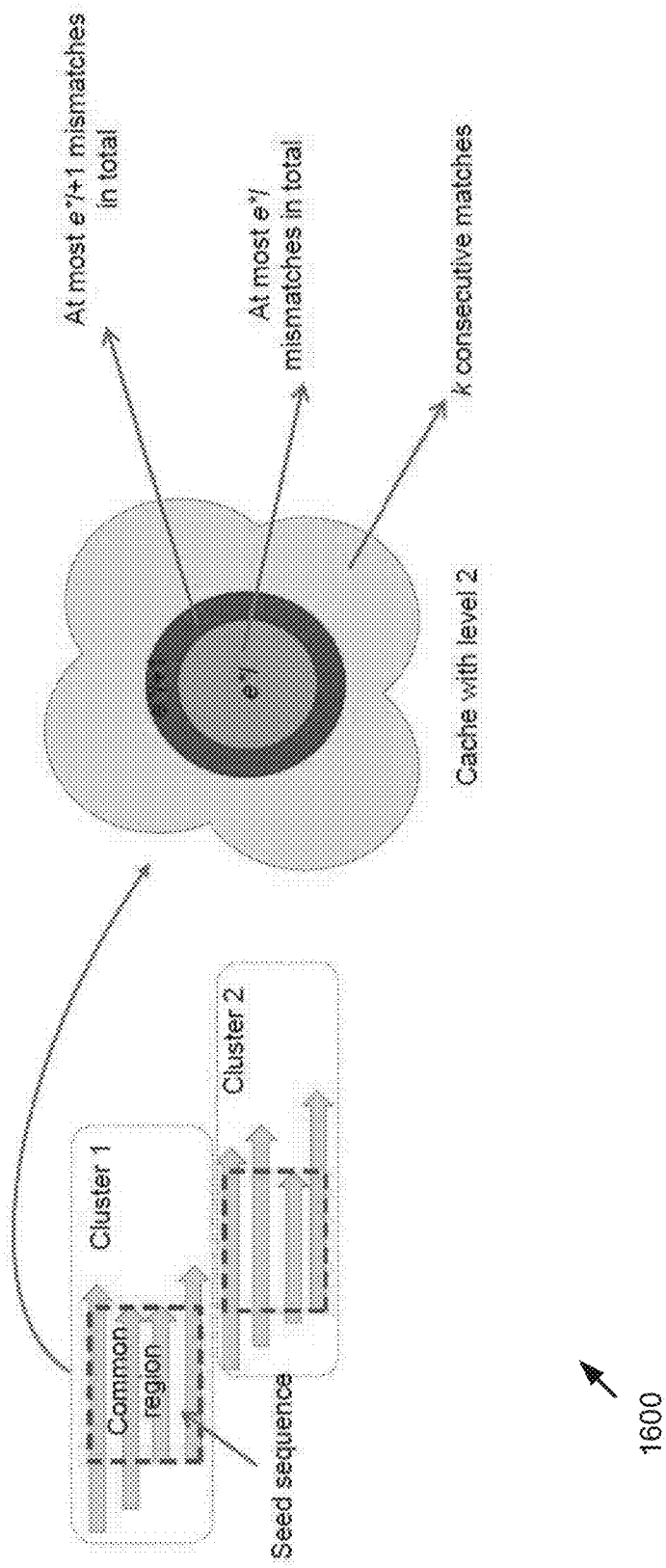
FIG. 16 is a block diagram showing a multi-level cache for common regions.

FIG. 16 is a block diagram showing caching for common regions. In the example, seed sequences were found for primer clusters. The seed sequences were extended to common regions. The multi-level cache stores calculations for common regions that have k consecutive matches. Therefore, such common regions can be considered to satisfy rule #1 without having to re-calculate for other primers.

The multi-level cache stores calculations for common regions that have at most e*l mismatches in total. Therefore, such common regions can be considered to fail rule #2 without having to re-calculate for other primers of length l. Another level of the cache stores calculations for common regions that have at most e*(l+1) mismatches in total. Therefore, such common regions can be considered to fail rule #2 without having to re-calculate for other primers of length l+1.

Figure 17:
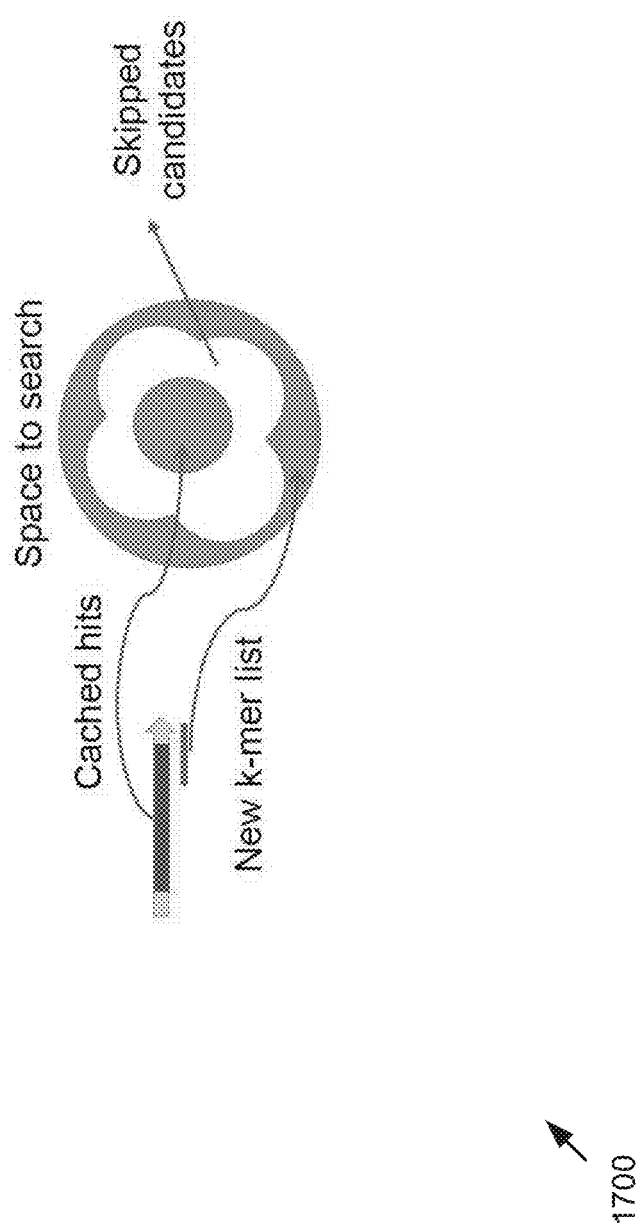
FIG. 17 is a block diagram showing skipped candidates via a cache.

FIG. 17 is a block diagram showing skipped candidates via a cache. In the example, the space to search includes those primer sequences having a common region that is determined to satisfy rules #1 and #2. Those that failed rule #2 can be safely skipped. A new k-mer list can be checked for the region of the primer sequence outside of the common region.

Figure 18:
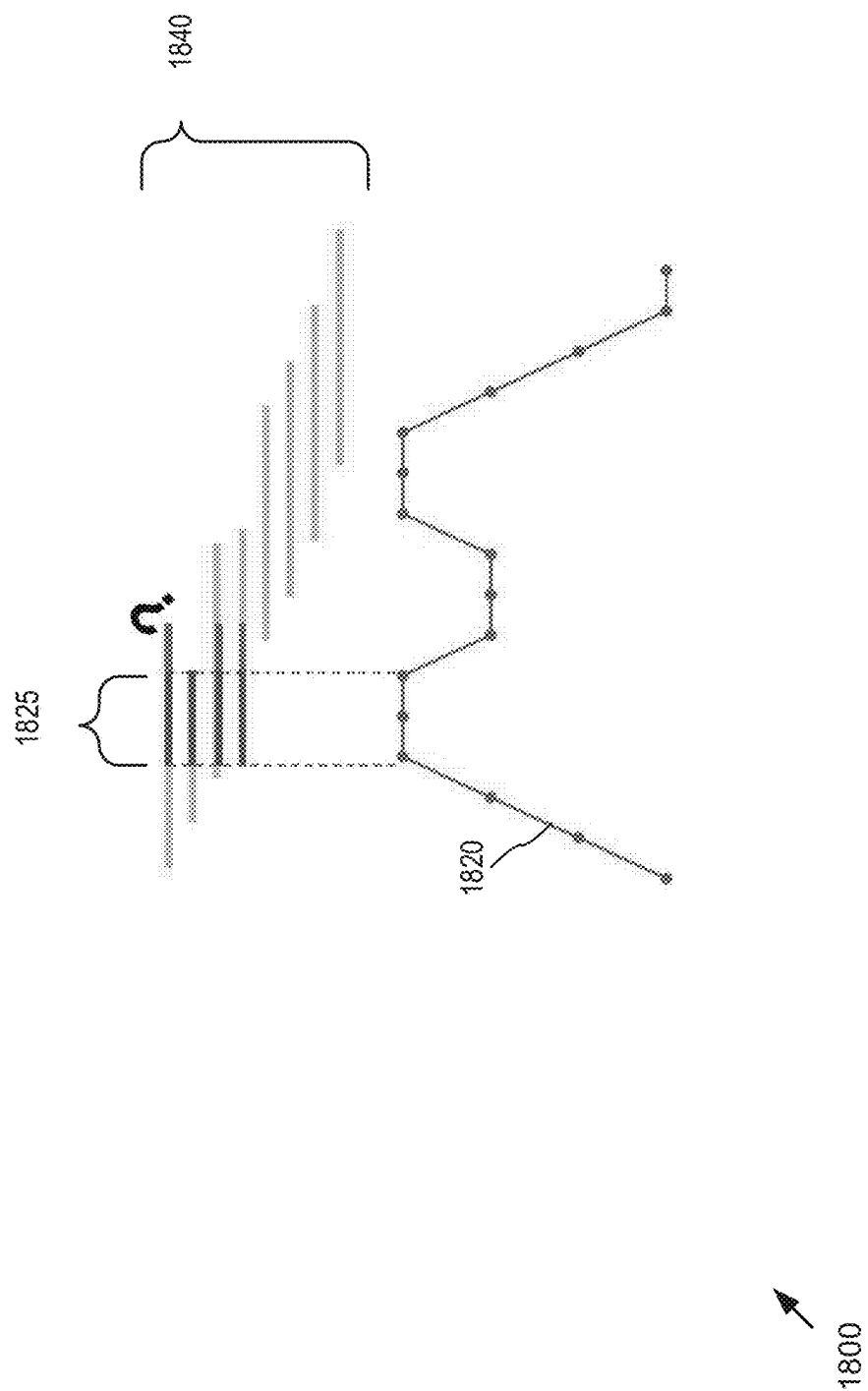
FIG. 18 is a block diagram showing extending a common region.

FIG. 18 is a block diagram showing an arrangement 1800 for extending a common region for clustered primer sequences 1840. The line 1820 on the lower portion of the figure reflects the number of primers that have identical nucleotides at a particular location of a primer (e.g., when the primers are aligned by overlapping regions). In the example, an initially discovered common region 1825 (e.g., sometimes called a "seed sequence") is being considered for extension. The number of primer sequences 1820 sharing the same value at a location can be considered as described herein when determining whether calculations will increase or decrease. In some cases, extending the common region 1825 will result in logically separate common regions, some of which are shared by different of the primers 1840.

Example 22—Example Implementation Results: Cache

Implementation of a cache allowed searching of some sequences with the cache. Some candidates could be verified or skipped via the cache, resulting in a 10-fold speedup in determination time.

A straightforward method did not use a cache, filtering, or sequence proximity groupings. Instead, the approach simply decomposed the primer into k-mers, searched a k-mer index for position lists, took the union of all the lists, and then verified the candidates to get final results. This approach could have been optimized with bit operation. Such an approach took 5.5 seconds per primer sequence on average, which resulted in 175 hours running time for 115,116 primer sequences (with 687 targets).

Figure 19:
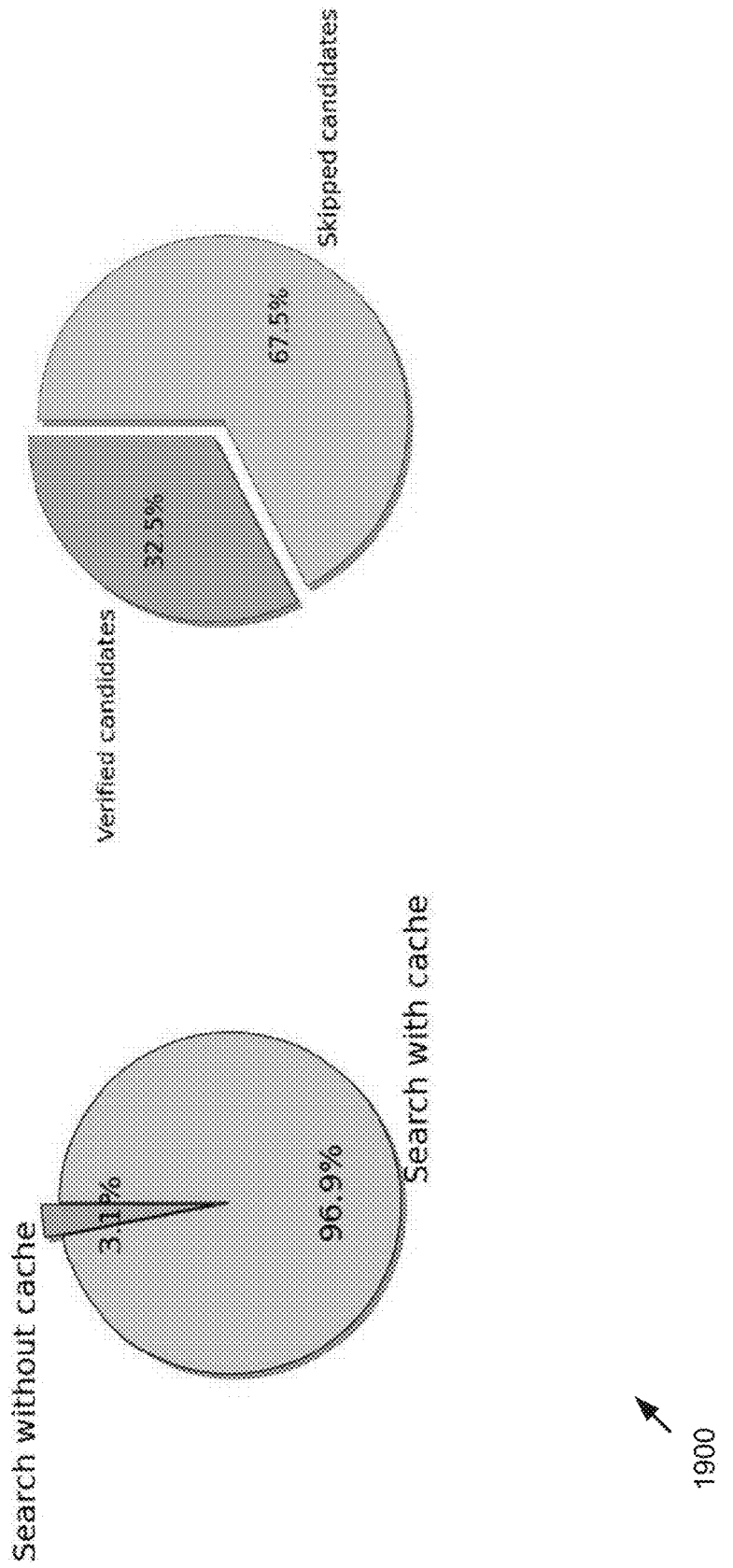
FIG. 19 is a block diagram showing results with a rule satisfaction cache.

FIG. 19 is a block diagram showing results with a rule satisfaction cache. In the example, 96.9% of sequences could be searched with the cache, of which 32.5% were verified candidates, and 67.5% were skipped candidates. The resulting time to complete the determination was 0.38 seconds per primer, resulting in a 10-fold speed up over 5.5 seconds per primer for the straightforward method (e.g., without cache).

Example 23—Example Implementation Results: Off-Target Prediction

Figure 20:
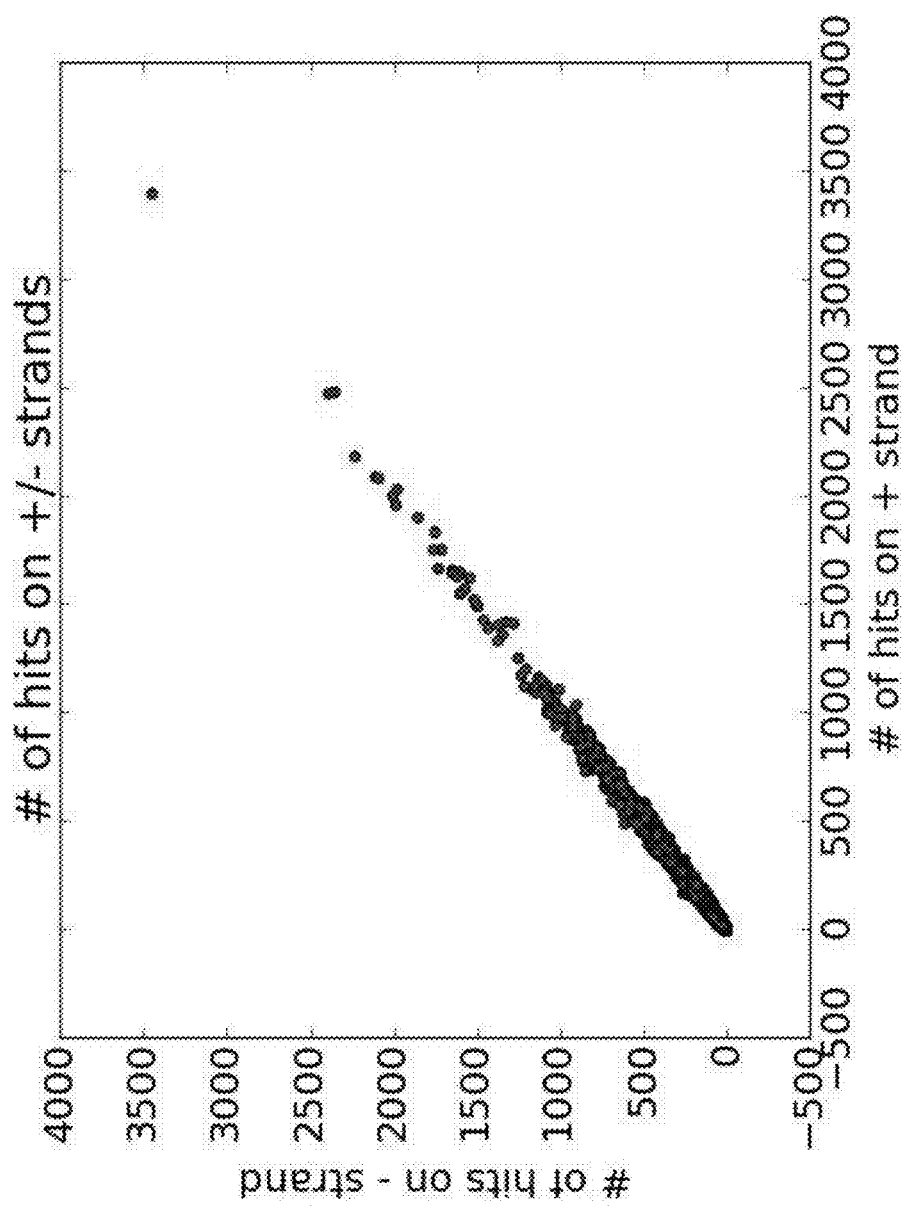
FIG. 20 is a block diagram showing correlation between hits on positive and negative strands of a reference genome.

FIG. 20 is a block diagram showing correlation between hits on positive and negative strands of a reference genome sequence. As shown, a primer's number of hits on the positive strand and the number of hits on the negative strand can be usually highly correlated, for example on the human genome. Therefore, a prediction for one strand can be used for both strands without negative consequences. Thus, the predictor as shown herein can generate a single prediction for a single strand and be used to filter candidate primer sequences without over or under filtering.

Figure 21:
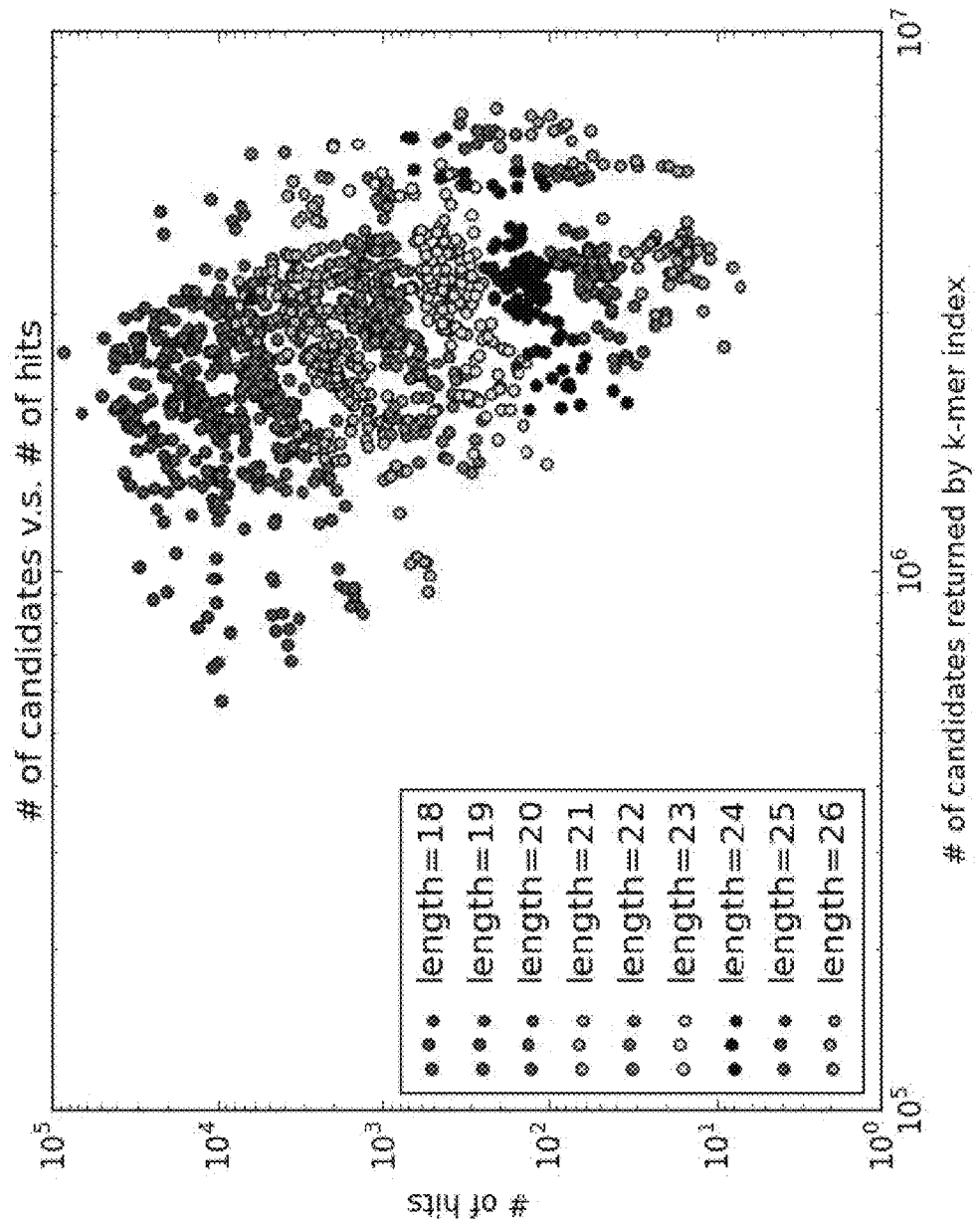
FIG. 21 is a block diagram showing correlation between number of candidates and number of hits for different sequence lengths.

FIG. 21 is a block diagram showing correlation between number of candidates and number of hits for different sequence lengths. As shown, correlation is present across different sequence lengths. The observed phenomenon of correlation between sequence length of the primer and number of actual hits on the reference genome sequence (e.g., for a variety of sequence lengths) can be used as a basis for constructing a predictor based on sequence length as described herein.

Figure 22:
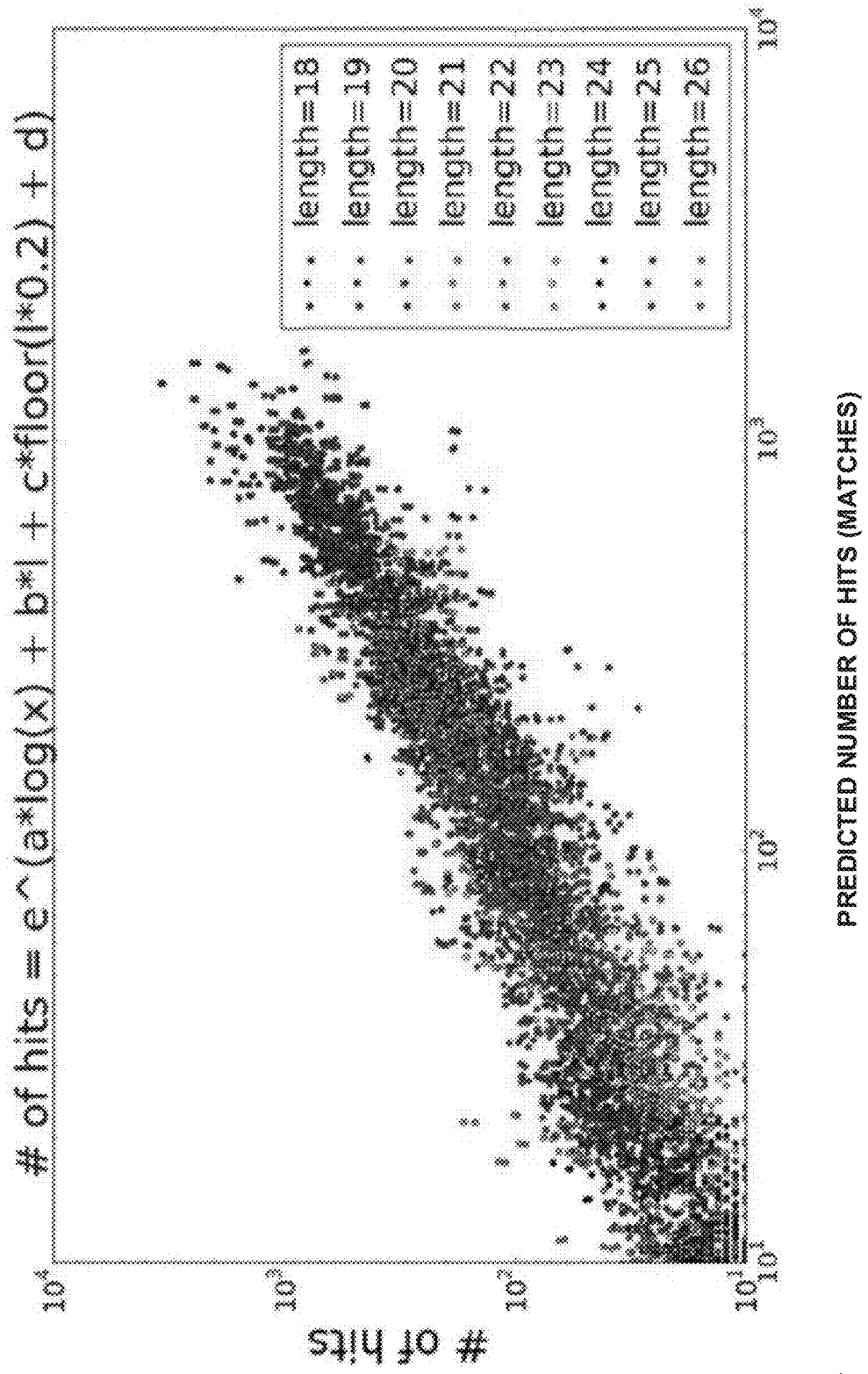
FIG. 22 is a block diagram showing historical data of number of hits versus a prediction using Calculation A.

FIG. 22 shows historical data of number of hits versus a prediction (e.g., predicted number of hits) using Calculation A described above. In the example, the human genome was used, and training resulted in the parameters shown. The parameters used were a=1.97, b=1.23, c=1.96, d=−4.43. Using such parameters, the number of matches (hits) for a primer can be predicted before searching for matches. The historical data establishes that the predictor is accurate due to the strong correlation between actual number of matches and predicted number of matches evident in the figure. The parameters can be derived based on historical data and may vary depending on which version of the genome is used.

Example 24—Further Combinations

Further, the technologies can be combined so that caching, filtering by match prediction, and sequence proximity groupings operate together. In such an example, a computer-implemented method of identifying off-target matches on a reference genome sequence comprises receiving a candidate primer sequence; for the candidate primer sequence, identifying a plurality of candidate matching locations on the reference genome sequence; out of the candidate matching locations, identifying verified matching locations on the reference genome sequence, wherein identifying verified matching locations comprises determining which of the candidate matching locations on the reference genome sequence satisfy one or more matching verification rules and reusing a rule satisfaction calculation already calculated for a different candidate primer sequence sharing a common region with the candidate primer sequence; and determining whether the verified matching locations form an off-target match condition on the reference genome sequence when considered in conjunction with at least one other match for at least one other candidate primer sequence; wherein the method further comprises filtering at least one additional candidate primer sequence, wherein the filtering comprises generating a prediction of a number of matches on the reference genome sequence for the additional candidate primer sequence and, responsive to determining that the number of matches exceeds a threshold, discarding the additional candidate primer sequence; wherein the method further comprises placing the verified matches into sequence proximity groupings; and checking the proximity groupings to identify the off-target match condition.

Example 25—Example Computing Systems

Figure 25:
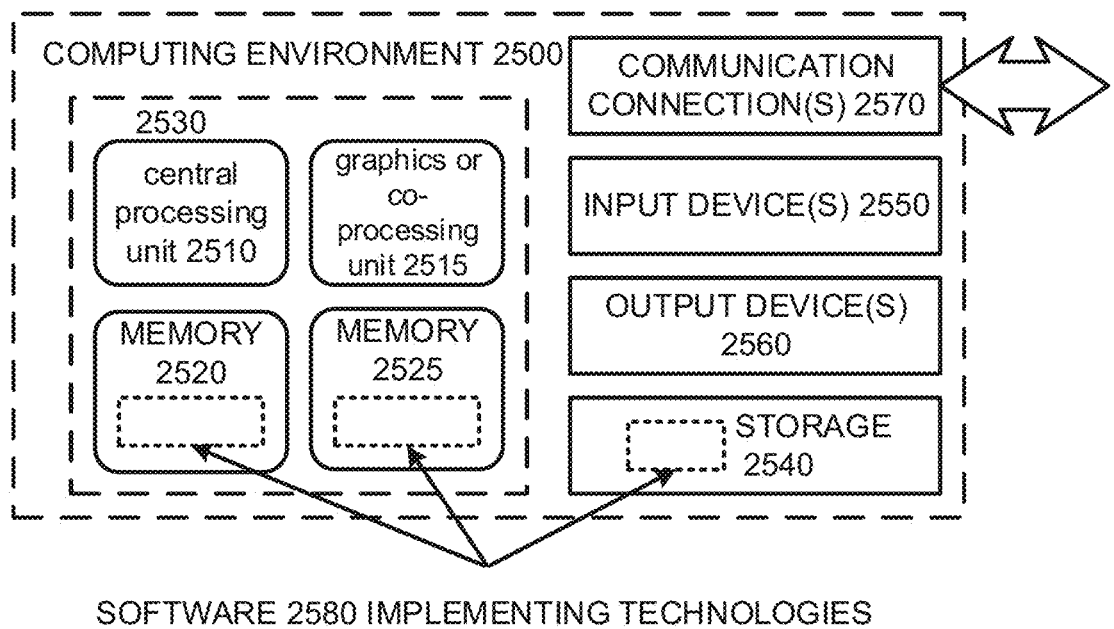
FIG. 25 is a diagram of an example computing system in which described embodiments can be implemented.

FIG. 25 illustrates a generalized example of a suitable computing system 2500 in which several of the described innovations may be implemented. The computing system 2500 is not intended to suggest any limitation as to scope of use or functionality, as the innovations may be implemented in diverse computing systems, including special-purpose computing systems. In practice, a computing system can comprise multiple networked instances of the illustrated computing system.

With reference to FIG. 25, the computing system 2500 includes one or more processing units 2510, 2515 and memory 2520, 2525. In FIG. 25, this basic configuration 2530 is included within a dashed line. The processing units 2510, 2515 execute computer-executable instructions. A processing unit can be a central processing unit (CPU), processor in an application-specific integrated circuit (ASIC), or any other type of processor. In a multi-processing system, multiple processing units execute computer-executable instructions to increase processing power. For example, FIG. 25 shows a central processing unit 2510 as well as a graphics processing unit or co-processing unit 2515. The tangible memory 2520, 2525 may be volatile memory (e.g., registers, cache, RAM), non-volatile memory (e.g., ROM, EEPROM, flash memory, etc.), or some combination of the two, accessible by the processing unit(s). The memory 2520, 2525 stores software 2580 implementing one or more innovations described herein, in the form of computer-executable instructions suitable for execution by the processing unit(s).

A computing system may have additional features. For example, the computing system 2500 includes storage 2540, one or more input devices 2550, one or more output devices 2560, and one or more communication connections 2570. An interconnection mechanism (not shown) such as a bus, controller, or network interconnects the components of the computing system 2500. Typically, operating system software (not shown) provides an operating environment for other software executing in the computing system 2500, and coordinates activities of the components of the computing system 2500.

The tangible storage 2540 may be removable or non-removable, and includes magnetic disks, magnetic tapes or cassettes, CD-ROMs, DVDs, or any other medium which can be used to store information in a non-transitory way and which can be accessed within the computing system 2500. The storage 2540 stores instructions for the software 2580 implementing one or more innovations described herein.

The input device(s) 2550 may be a touch input device such as a keyboard, mouse, pen, or trackball, a voice input device, a scanning device, or another device that provides input to the computing system 2500. For video encoding, the input device(s) 2550 may be a camera, video card, TV tuner card, or similar device that accepts video input in analog or digital form, or a CD-ROM or CD-RW that reads video samples into the computing system 2500. The output device(s) 2560 may be a display, printer, speaker, CD-writer, or another device that provides output from the computing system 2500.

The communication connection(s) 2570 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Example 26—Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing device to perform the method. The technologies described herein can be implemented in a variety of programming languages.

ALTERNATIVES

The technologies from any example can be combined with the technologies described in any one or more of the other examples. In view of the many possible embodiments to which the principles of the disclosed technology may be applied, it should be recognized that the illustrated embodiments are examples of the disclosed technology and should not be taken as a limitation on the scope of the disclosed technology. Rather, the scope of the disclosed technology includes what is covered by the following claims. All that comes within the scope and spirit of the claims is therefore claimed.

The invention claimed is:

1. A computer-implemented method of identifying off-target matches from a set of candidate primer sequences on a genome reference sequence, the method comprising:
   receiving onto a data storage unit a plurality of candidate primer sequences, wherein some or all of the plurality of candidate primer sequences are organized into clusters, wherein each cluster comprises a respective common region shared by candidate primer sequences within the respective cluster;
   populating or updating a cache with one or more respective rule satisfaction calculations for respective common regions when they are initially evaluated as candidate matches or verified matches;
   for each candidate primer sequence, calculating using a processor a plurality of candidate matches on the genome reference sequence for the candidate primer sequences, wherein calculating the plurality of candidate matches comprises reusing one or more rule satisfaction calculations for common regions when present in the cache;
   calculating, using the processor, verified matches on the genome reference sequence based on the candidate matching locations satisfying a plurality of matching verification rules, wherein calculating the verified matches comprises reusing one or more rule satisfaction calculations for common regions when present in the cache;
   performing matching calculations of the verified matches, using the processor, to determine whether the verified matches form an off-target match condition on the genome reference sequence; and
   generating a location profile on the genome reference sequence based on the off-target match condition from the verified matches that meet a predetermined off-target threshold.

2. The method of claim 1, wherein:
the cache supports multiple levels that are calculated for respective different lengths of candidate primer sequences.

3. The method of claim 2 further comprising:
calculating a computing expense for building the cache; and
extending one or more common regions based on a balance of resources saved by using the cache and resources used by building the cache.

4. The method of claim 1 further comprising:
determining whether the candidate primer sequence is an acceptable sequence based on whether the verified matches form an off-target match condition on the reference genome sequence.

5. The method of claim 1, wherein the candidate matches comprise a candidate matching location of the corresponding candidate primer sequence on the genome reference sequence, and
wherein the verified matches comprise a verified matching location of the verified matches on the genome reference sequence.

6. The method of claim 1, wherein the plurality of candidate primer sequences comprises a first candidate primer sequence, the method further comprising:
generating a prediction of a number of matches on the reference genome sequence for the first candidate primer sequence;
responsive to determining that the predicted number of matches exceeds a threshold, discarding the first candidate primer sequence before the calculating.

7. The method of claim 1 further comprising:
clustering a plurality of sequences corresponding to the verified matches into sequence proximity groupings; and
checking the sequence proximity groupings to identify the off-target match condition.

8. The method of claim 7 wherein:
checking the sequence proximity groupings comprises checking matches in neighboring groupings.

9. A computing system for identifying off-target matches from a set of candidate primer sequences on a genome reference sequence, the computing system comprising:
   at least one processor; and
   a memory storing instructions that, when executed by the at least one processor, causes the computing system to perform:
      receiving onto a data storage unit a plurality of candidate primer sequences, wherein some or all of the plurality of candidate primer sequences are organized into clusters, wherein each cluster comprises a respective common region shared by candidate primer sequences within the respective cluster;
      populating or updating a cache with one or more respective rule satisfaction calculations for respective common regions when they are initially evaluated as candidate matches or verified matches;
      for each candidate primer sequence, calculating a plurality of candidate matches on the genome reference sequence for the candidate primer sequences, wherein calculating the plurality of candidate matches comprises reusing one or more rule satisfaction calculations for common regions when present in the cache;
      calculating verified matches on the genome reference sequence based on the candidate matching locations satisfying a plurality of matching verification rules, wherein calculating the verified matches comprises reusing one or more rule satisfaction calculations for common regions when present in the cache;
      performing matching calculations of the verified matches to determine whether the verified matches form an off-target match condition on the genome reference sequence; and
      generating a location profile on the genome reference sequence based on the off-target match condition from the verified matches that meet a predetermined off-target threshold.

10. The computing system of claim 9, wherein:
the cache is coupled to the memory, and
wherein the cache stores rules satisfaction calculations separately for different parameters of a respective rule.

11. The computing system of claim 10 wherein the memory further stores instructions that when executed by the at least one processor causes the computer system to perform skipping a rule satisfaction calculation for at least one of the candidate primer sequences based on the cache.

12. The computing system of claim 10 wherein:
the cache supports multiple levels that are calculated for respective different lengths of candidate primer sequences.

13. The computing system of claim 9 wherein the memory further stores instructions that when executed by the at least one processor causes the computer system to perform:
calculating a computing expense for building the cache; and
extending the common region based on a balance of resources saved by using the cache and resources used by building the cache.

14. The computing system of claim 9 wherein the memory further stores instructions that when executed by the at least one processor causes the computer system to perform:
determining whether the candidate primer sequence is an acceptable sequence based on whether the verified matches form an off-target match condition on the reference genome sequence.

15. The computing system of claim 9, wherein the candidate matches comprise a candidate matching location of the corresponding candidate primer sequence on the genome reference sequence, and
wherein the verified matches comprise a verified matching location of the verified matches on the genome reference sequence.

16. The computing system of claim 9, wherein the plurality of candidate primer sequences comprises a first candidate primer sequence, and wherein the memory further stores instructions that when executed by the at least one processor causes the computer system to perform:
generating a prediction of the number of matches on the reference genome sequence for the first candidate primer sequence;
responsive to determining that the predicted number of matches exceeds a threshold, discarding the first candidate primer sequence before the calculating.

17. The computing system of claim 9, wherein the memory further stores instructions that when executed by the at least one processor causes the computer system to perform:
clustering a plurality of sequences corresponding to the verified matches into sequence proximity groupings; and
checking the sequence proximity groupings to identify the off-target match condition.

18. A non-transitory computer-readable storage medium for identifying off-target matches from a set of candidate primer sequences on a genome reference sequence comprising computer-executable instructions that when executed cause a computing system to:
receive onto a data storage unit a plurality of candidate primer sequences, wherein some or all of the plurality of candidate primer sequences are organized into clusters, wherein each cluster comprises a respective common region shared by candidate primer sequences within the respective cluster;
populate or update a cache with one or more respective rule satisfaction calculations for respective common regions when they are initially evaluated as candidate matches or verified matches;
for each candidate primer sequence, calculate a plurality of candidate matches on the genome reference sequence for the candidate primer sequences, wherein calculating the plurality of candidate matches comprises reusing one or more rule satisfaction calculations for common regions when present in the cache;
calculate verified matches on the genome reference sequence based on the candidate matching locations satisfying a plurality of matching verification rules, wherein calculating the verified matches comprises reusing one or more rule satisfaction calculations for common regions when present in the cache;
perform matching calculations of the verified matches to determine whether the verified matches form an off-target match condition on the genome reference sequence; and
generate a location profile on the genome reference sequence based on the off-target match condition from the verified matches that meet a predetermined off-target threshold.

* * * * *

UNITED STATES PATENT AND TRADEMARK OFFICE
CERTIFICATE OF CORRECTION

PATENT NO.       : 10,971,249 B2  
APPLICATION NO.  : 15/705079  
DATED            : April 6, 2021  
INVENTOR(S)      : Honglei Liu and Jocelyne Bruand It is certified that error appears in the above-identified patent and that said Letters Patent is hereby corrected as shown below:

On the Title Page

Item [56], Column 2, Line 3:
Delete "courrsera.org," and insert -- coursera.org, --, therefor.

Item [56], Column 2, Line 5:
Delete "courrsera.org," and insert -- coursera.org, --, therefor.

In the Claims

Column 25, Line 1:
Claim 10, delete "rules" and insert -- rule --, therefor.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*